(12) United States Patent
Weiss

(10) Patent No.: US 6,458,164 B1
(45) Date of Patent: Oct. 1, 2002

(54) ARTIFICIAL HEART WITH ENERGY RECOVERY

(75) Inventor: William J. Weiss, Mechanicsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 09/557,811

(22) Filed: Apr. 25, 2000

(51) Int. Cl.$^7$ ................................................ A61M 1/12
(52) U.S. Cl. ........................ 673/3.27; 623/3.28; 600/17; 607/61
(58) Field of Search ................................ 623/3.1, 3.27, 623/3.28; 600/16, 17; 607/33, 34, 60, 61, 65

(56) References Cited

U.S. PATENT DOCUMENTS

| | | |
|---|---|---|
| 3,942,535 A | 3/1976 | Schulman |
| 4,143,661 A | 3/1979 | LaForge et al. |
| 4,221,543 A | 9/1980 | Cosentino et al. |
| 4,233,546 A | 11/1980 | Berthiaume |
| 4,237,895 A | 12/1980 | Johnson |
| 4,263,642 A | 4/1981 | Simmons et al. |
| 4,417,349 A | 11/1983 | Hills et al. |
| 4,439,806 A | 3/1984 | Brajder |
| 4,446,513 A | 5/1984 | Clenet |
| 4,453,537 A | 6/1984 | Spitzer |
| 4,532,932 A | 8/1985 | Batty, Jr. |
| 4,561,443 A | 12/1985 | Hogrefe et al. |
| 4,625,730 A | 12/1986 | Fountain et al. |
| 4,665,896 A | 5/1987 | LaForge et al. |
| 4,691,270 A | 9/1987 | Pruitt |
| 4,706,689 A | 11/1987 | Man |
| 4,855,888 A | 8/1989 | Henze et al. |
| 4,925,443 A | 5/1990 | Heilman et al. |
| 4,933,798 A | 6/1990 | Widmayer et al. |
| 4,941,201 A | 7/1990 | Davis |
| 4,941,652 A | 7/1990 | Nagano et al. |
| 4,947,844 A | 8/1990 | McDermott |
| 4,953,068 A | 8/1990 | Henze |
| 4,964,027 A | 10/1990 | Cook et al. |
| 4,979,506 A | 12/1990 | Silvian |
| 5,132,888 A | 7/1992 | Lo et al. |
| 5,132,889 A | 7/1992 | Hitchcock et al. |

(List continued on next page.)

FOREIGN PATENT DOCUMENTS

EP  0 412 422 A2  2/1991

OTHER PUBLICATIONS

Nazarian et al., "Development of a Totally Implantable Artificial Heart Concept to Implementation", *IEEE Case Studies in Medical Instrument Design*, pp. 95–110.

Snyder et al., "Microcomputer Control of Permanently Implanted Blood Pumps", *Computer Society Press Reprint*, pp. 154–157.

Primary Examiner—David H. Willse
(74) Attorney, Agent, or Firm—Marshall, Gerstein & Borun.

(57) ABSTRACT

An apparatus for use in an artificial heart assembly includes an internal coil adapted to be implanted beneath the skin of a subject and an external coil coupled to transmit electric power to the internal coil through the skin of the subject. The apparatus includes a DC-to-AC converter coupled to the external coil which selectively converts DC power from a DC power source into either a first frequency or a second frequency, the first frequency having a plurality of cycles each of a first duration and the second frequency having a plurality of cycles each of a second duration longer than the first duration. The DC-to-AC converter comprises four switching components each coupled in parallel with a respective one of four passive components and a drive circuit operatively coupled to the switching components. The drive circuit causes the switching components to be switched to a nonconductive state so that they are nonconductive for a time period and so that electric current flows through a plurality of the passive components during that time period.

19 Claims, 17 Drawing Sheets

U.S. PATENT DOCUMENTS

| | | |
|---|---|---|
| 5,157,593 A | 10/1992 | Jain |
| 5,279,292 A | 1/1994 | Baumann et al. |
| 5,314,457 A | 5/1994 | Jeutter et al. |
| 5,327,335 A | 7/1994 | Maddali et al. |
| 5,345,375 A | 9/1994 | Mohan |
| 5,350,413 A | 9/1994 | Miller |
| 5,400,235 A | 3/1995 | Carroll |
| 5,438,498 A | 8/1995 | Ingemi |
| 5,444,608 A | 8/1995 | Jain et al. |
| 5,499,178 A | 3/1996 | Mohan |
| 5,515,264 A | 5/1996 | Stacey |
| 5,522,865 A | 6/1996 | Schulman et al. |
| 5,532,919 A | 7/1996 | Gegner |
| 5,559,689 A | 9/1996 | Kirchberg et al. |
| 5,569,156 A | 10/1996 | Mussivand |
| 5,569,307 A | 10/1996 | Schulman et al. |
| 5,584,870 A | 12/1996 | Single et al. |
| 5,594,635 A | 1/1997 | Gegner |
| 5,630,836 A | 5/1997 | Prem et al. |
| 5,674,281 A | 10/1997 | Snyder |
| 5,702,431 A | 12/1997 | Wang et al. |
| 5,704,891 A | 1/1998 | Mussivand |
| 5,713,939 A | 2/1998 | Nedungadi et al. |
| 5,728,154 A | 3/1998 | Crossett et al. |
| 5,741,314 A | 4/1998 | Daly et al. |
| 5,749,909 A | 5/1998 | Schroeppel et al. |
| 5,751,125 A | 5/1998 | Weiss |
| 5,781,419 A | 7/1998 | Kutkut et al. |
| 6,240,318 B1 * | 5/2001 | Phillips ................ 607/61 |
| 6,345,203 B1 * | 2/2002 | Mueller et al. ........... 607/60 |

* cited by examiner

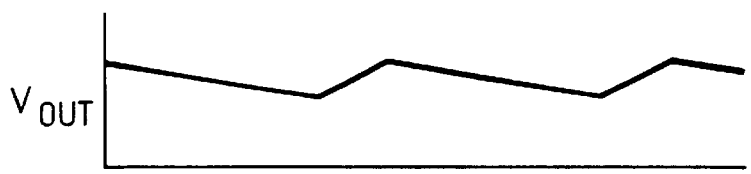
FIG. 7A
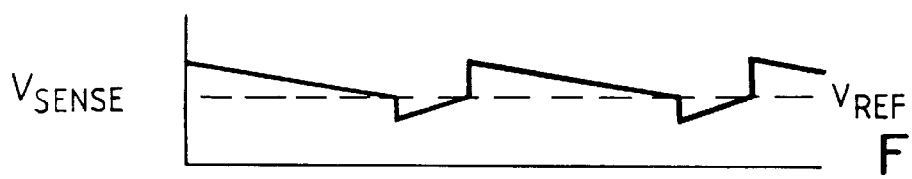
FIG. 7B
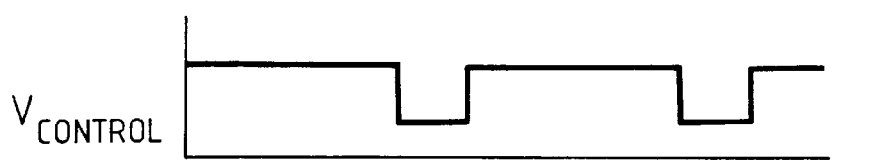
FIG. 7C
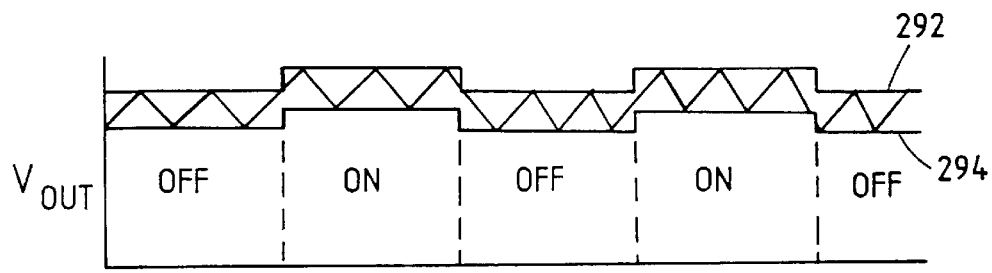
FIG. 8
FIG. 9A
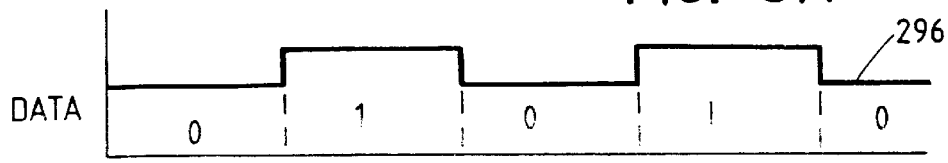
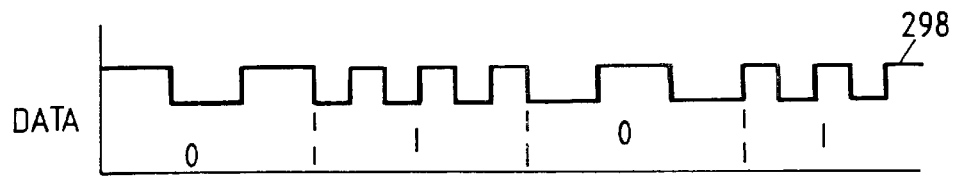
FIG. 9B

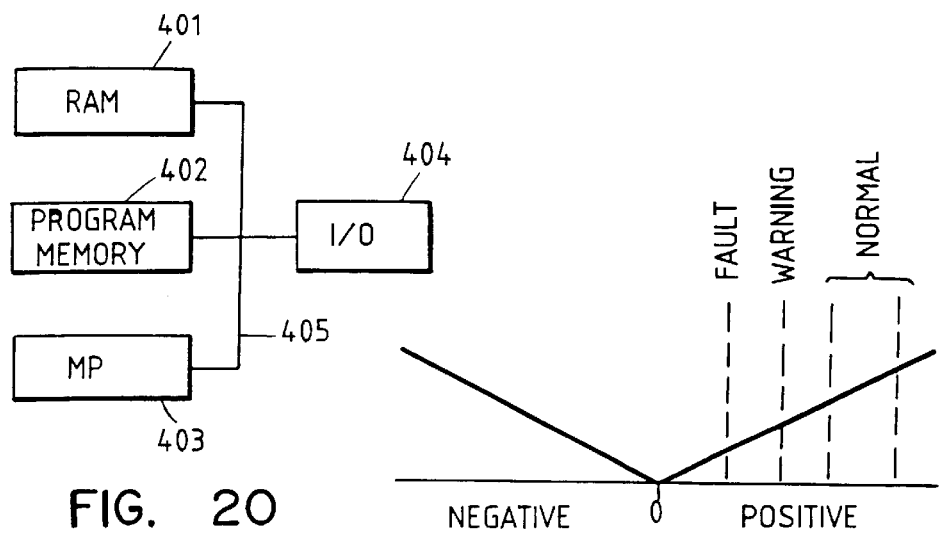
FIG. 20
FIG. 21
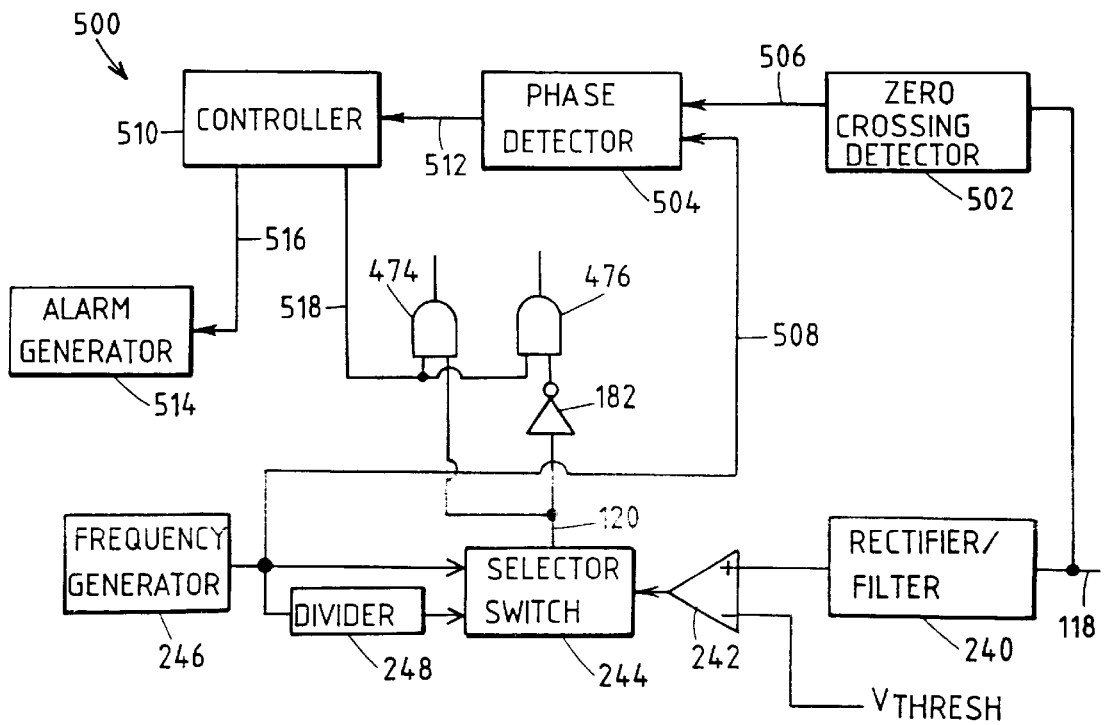
FIG. 22

ARTIFICIAL HEART WITH ENERGY RECOVERY

This patent is subject to Government Contract No. N01-HV-38130 with the National Institutes of Health.

BACKGROUND OF THE INVENTION

The present invention is directed to an artificial heart apparatus with an energy recovery circuit.

U.S. Pat. No. 5,674,281 to Snyder discloses an artificial heart assembly having a blood inlet conduit, a blood outlet conduit, and a pumping mechanism that pumps blood from the blood inlet conduit to the blood outlet conduit. The Snyder artificial heart assembly includes a first membrane defining a blood chamber fluidly coupled to the blood inlet conduit and the blood outlet conduit, and the pumping mechanism includes a pusher plate that makes contact with the first membrane to force blood from the blood inlet conduit to the blood outlet conduit. The Snyder artificial heart assembly also has a second membrane defining a second blood chamber fluidly coupled to a second blood inlet conduit and a second blood outlet conduit and a second pusher plate that makes contact with the second membrane to force blood from the second blood inlet conduit to the second blood outlet conduit.

U.S. Pat. No. 5,728,154 to Crossett, et al. discloses an artificial heart assembly that has a structure similar to the artificial heart assembly described above in connection with the Snyder patent. The Crossett, et al. patent also discloses a communications system that includes an external transceiver located external of a subject and an internal transceiver that is implanted beneath the skin of a subject. The internal transceiver is provided with an internal coil.

U.S. Pat. No. 5,751,125 to Weiss discloses an artificial heart assembly, which is provided either as a total artificial heart or as a ventricular assist device, having a sensorless motor and a circuit for reversibly driving the sensorless motor.

U.S. Pat. No. 5,630,836 to Prem, et al. discloses a transcutaneous energy and data transmission apparatus for a cardiac assist device such as an artificial heart or ventricular assist device. The transmission apparatus has an external coupler in the form of a tuned circuit with an induction coil and an internal coupler which together act as an air-core transformer. The transmission apparatus has a DC power supply and a power converter that are coupled to the external coupler. The power converter converts electric current from the DC power supply into high-frequency AC. The transmission apparatus has a voltage regulator coupled to the internal coupler. As shown in FIG. 3 and described in connection therewith, the Prem, et al. patent discloses that the voltage regulator includes a shunt switch and a shunt controller. As shown in FIG. 2, the power converter includes an H-bridge inverter, an H-bridge controller, and a shunt detector. The H-bridge controller can reduce the duty cycle of the H-bridge converter if a shunt is detected.

SUMMARY OF THE INVENTION

The invention is directed to an apparatus for use in an artificial heart assembly having a blood inlet conduit, a blood outlet conduit, and a pump that is adapted to pump blood from the blood inlet conduit to the blood outlet conduit. The apparatus includes an internal coil adapted to be implanted beneath the skin of a subject and an external coil adapted to be disposed adjacent the internal coil and separated from the internal coil by the skin of the subject, the external coil being coupled to transmit electric power to the internal coil through the skin of the subject.

The apparatus includes a DC-to-AC converter coupled to the external coil and to a source of DC power. The DC-to-AC converter selectively converts DC power from the DC power source into either a first frequency or a second frequency, the first frequency having a plurality of cycles each of a first duration and the second frequency having a plurality of cycles each of a second duration longer than the first duration.

The DC-to-AC converter comprises a first switching component coupled in parallel with a first passive component, a second switching component coupled in parallel with a second passive component, a third switching component coupled in parallel with a third passive component, a fourth switching component coupled in parallel with a fourth passive component, and a drive circuit operatively coupled to the switching components. The drive circuit causes all four of the switching components to be switched to a nonconductive state so that the four switching components are nonconductive for a time period and so that electric current flows through a plurality of the passive components during that time period.

The drive circuit may cause all four of the switching components to be switched to a nonconductive state for a time period at least as long as the first duration, or for a time period at least twice as long as the first duration.

The first switching component may be connected to the second switching component at a first junction, the second switching component may be connected to the third switching component at a second junction, the third switching component may be connected to the fourth switching component at a third junction, and the fourth switching component may be connected to the first switching component at a fourth junction. The fourth junction may be connected to the DC power source, the second junction may be connected to a ground potential, and the external coil may be connected between the first and third junctions. The switching components may comprise transistors, and the passive components may comprise diodes.

The features and advantages of the present invention will be apparent to those of ordinary skill in the art in view of the detailed description of the preferred embodiment, which is made with reference to the drawings, a brief description of which is provided below.

BRIEF DESCRIPTION OF THE DRAWINGS

FIGS. 7A–7C illustrate various voltage waveforms generated during operation of the power circuit;

FIG. 8 illustrates the change in the voltage on a power supply capacitor induced by a voltage modulating circuit;

FIGS. 9A–9B illustrate a number of data waveforms;

FIG. 20 is a block diagram of a controller;

FIG. 21 is a graph illustrating a range of phase shifts between voltage and current;

FIG. 22 illustrates an embodiment of a metal detection and power supply circuit;

DETAILED DESCRIPTION OF VARIOUS EMBODIMENTS

Figure 1:
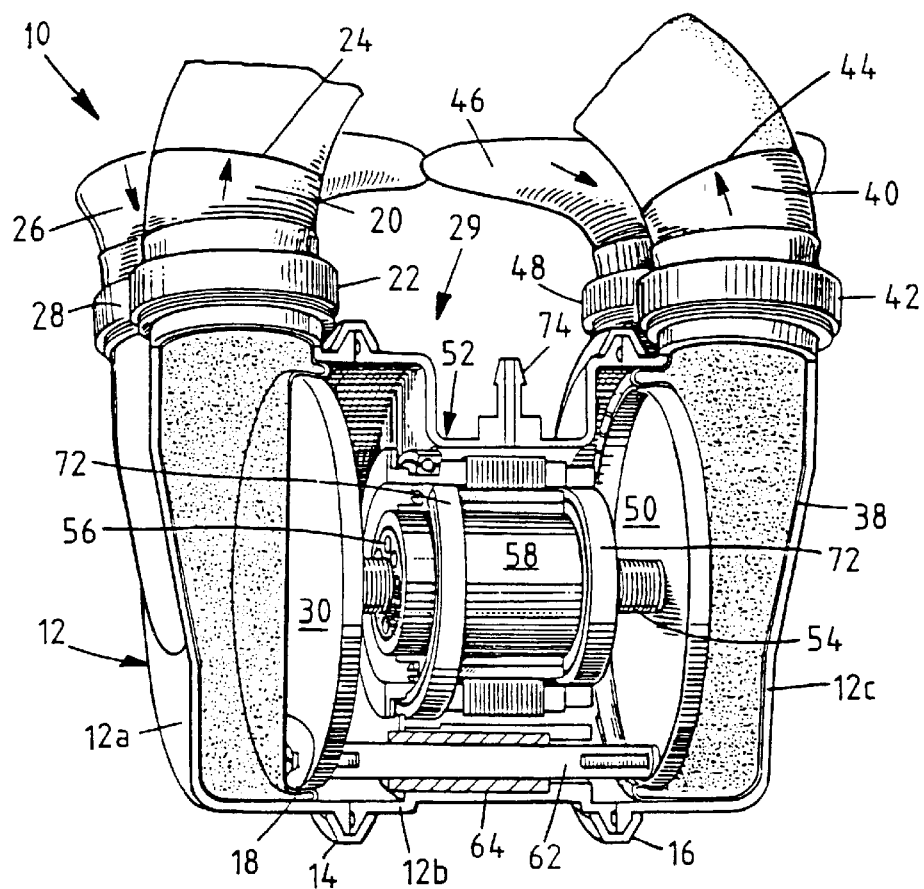
FIG. 1 is a perspective view of the mechanical portions of an artificial heart assembly, portions of which are shown in cross section.

FIG. 1 illustrates the mechanical portions of an artificial heart assembly 10 which may be implanted within a subject, such as a human or an animal, to take the place of the subject's natural heart. As defined herein, an artificial heart assembly intended for use with a subject, such as an animal or human, may be a total artificial heart (TAH) intended to replace the entire heart of the subject, a ventricular assist device (VAD) intended to replace a portion of the subject's heart, or an external blood pump to be used with the subject.

The artificial heart assembly 10 has a housing 12 composed of three sections 12a, 12b, 12c which are held together by a pair of annular V-rings 14, 16. A blood reservoir within a sac 18 disposed within the housing section 12a is fluidly coupled to a blood outlet defined by an artificial vascular graft 20 connected to the housing section 12a via a threaded connector 22. The graft 20 may be connected to the pulmonary artery of the subject via a suture line 24. The blood reservoir within the sac 18 may be fluidly coupled to a blood inlet chamber defined by an artificial graft 26 which may be connected to the housing section 12a via a threaded connector 28 and to the right atrium of the subject via a suture line (not shown). A pair of one-way check valves (not shown) may be disposed in the blood inlet 26 and the blood outlet 20 to ensure that blood is pumped in the direction shown by the arrows in FIG. 1.

A blood sac 38 disposed within the housing section 12c may be fluidly coupled to a blood outlet defined by an artificial graft 40 connected to the housing section 12c via a threaded connector 42. The graft 40 may be connected to the aorta of the subject via a suture line 44. The blood reservoir in the blood sac 38 may be coupled to a blood inlet chamber defined by an artificial graft 46 which is connected to the housing section 12c via a threaded connector 48 and to the left atrium of the subject via a suture line (not shown). A pair of one-way check valves (not shown) may be disposed in the blood inlet 46 and the blood outlet 40 to ensure that blood is pumped in the direction shown by the arrows.

A pumping mechanism or pump 29 may be provided to pump blood from the blood inlet 26 to the blood outlet 20 and from the blood inlet 46 to the blood outlet 40. The pumping mechanism 29 has a pumping structure and a motor operatively coupled to drive the pumping structure. The pumping structure may be provided, for example, in the form of a pusher plate 30 that makes contact with and periodically deforms the blood sac 18 to force blood from the blood inlet 26 to the blood outlet 20 and a pusher plate 50 that makes contact with and periodically deforms the blood sac 38 to force blood from the blood inlet 46 to the blood outlet 40.

The pump 29 may include a DC brushless motor 52 that drives the pusher plates 30, 50 laterally back and forth. The motor 52 may be coupled to the pusher plates 30, 50 via a drive screw 54 and a coupling mechanism composed of a plurality of threaded elongate rollers 56 disposed within a cylindrical nut 58 fixed to a rotor (not shown) of the motor 52. Rotation of the rotor causes the nut 58 and rollers 56 to rotate, thus causing the drive screw 54 to be linearly displaced in a direction parallel to its longitudinal central axis. A guide rod 62 may be connected between the two pusher plates 30, 50 to pass through a fixed bushing 64 to prevent the plates 30, 50 from rotating. Other mechanisms for coupling the rotor to the pusher plates 30, 50 could be used.

The rotation of the rotor may be controlled via the electrical energization of a plurality of windings of a stator (not shown) which is rotatably coupled to the rotor via a pair of cylindrical bearings 72. A wire port 74 may be formed in the housing section 12b to allow the passage of wires from the windings to a controller 76 (FIG. 3), which may be implanted in another area of the subject, such as in the subject's abdomen.

The structural details of the artificial heart assembly 10 and the pumping mechanism 29 described above are exemplary only and are not considered important to the invention. Alternative designs could be utilized without departing from the invention.

Overall Assembly

Figure 3:
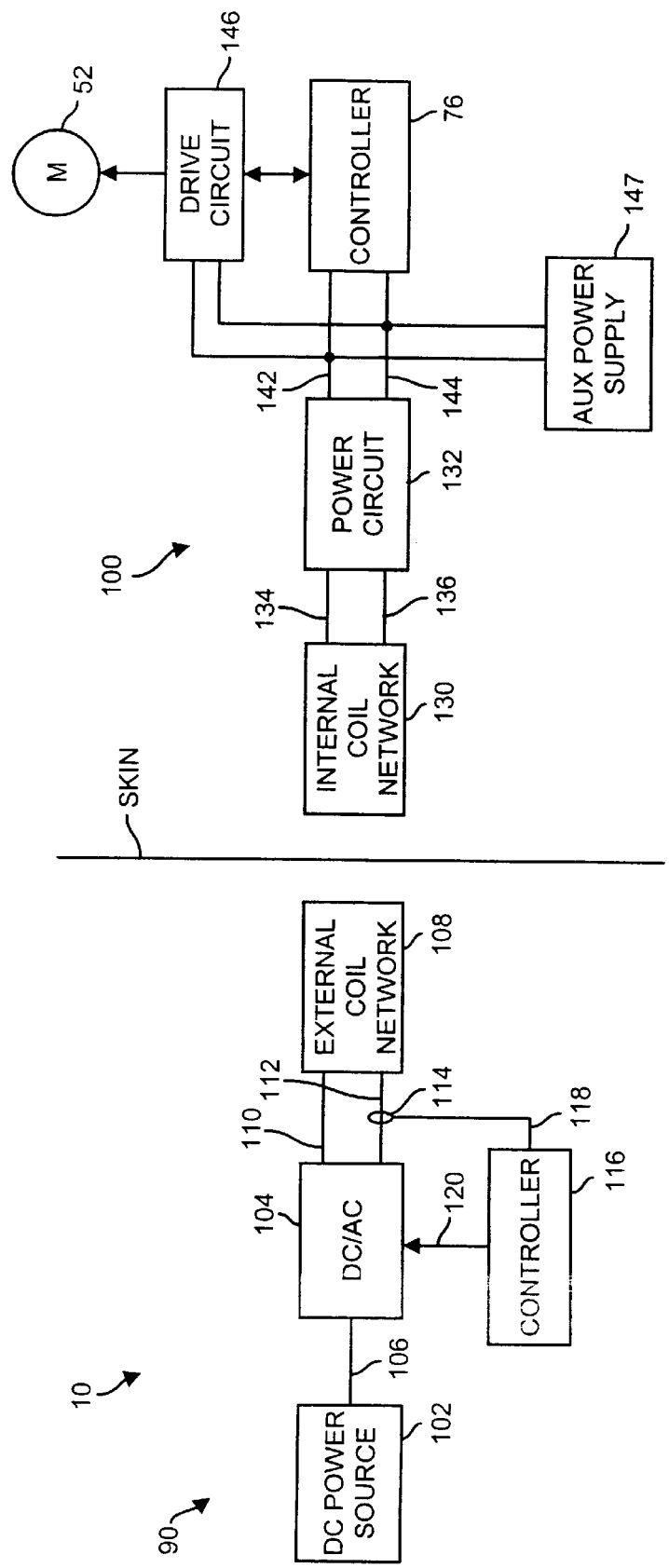
FIG. 3 is an overall block diagram of an embodiment of the electrical portions of an artificial heart assembly.

FIG. 3 is an overall block diagram of the electrical portions of the artificial heart assembly 10. Referring to FIG. 3, the artificial heart assembly 10 has an external assembly 90 that is provided at an external location outside of a subject and an internal assembly 100 that is implanted within the subject.

The external assembly 90 includes a DC power source 102 and a DC-to-AC converter 104 connected to the DC power source via a conductive line 106. The DC power source 102, which may be a portable battery or battery pack providing a DC voltage of between 10 and 18 volts, for example, supplies a DC voltage to the DC-to-AC converter 104, which converts that DC voltage into a high-frequency voltage. That high-frequency voltage is provided to an external coil network 108 via a pair of conductors 110, 112.

A current sensor schematically shown and designated 114 may be used to sense the magnitude of the electric current flowing within the conductor 112, and a controller 116 connected to the current sensor 114 via a conductor 118 may be used to control the operation of the DC-to-AC converter 104, via a control line 120, based on one or more characteristics of the current sensed by the sensor 114.

The external coil network 108, which is disposed adjacent the skin of the subject, transfers electric power through the skin of the subject to an internal coil network 130 disposed beneath the skin of the subject. The internal coil network 130 is connected to a power circuit 132 via a pair of conductors 134, 136, and the power circuit 132 supplies electric power to the controller 76 via a pair of conductors 142, 144. The controller 76 may control the operation of the motor 52 through a motor drive circuit 146. The power conductors 142, 144 also supply electric power to the motor 52 through the drive circuit 146.

The internal assembly 100 could also include an auxiliary power supply circuit 147 having a rechargeable battery, such as the circuit disclosed in U.S. Ser. No. 09/557,819 filed herewith and entitled "Artificial Heart With Arrhythmia Signalling" for which Alan Snyder is the named inventor.

The motor drive circuit 146 could be composed of a commutator (not shown) and a driver circuit (not shown), as disclosed in U.S. Pat. No. 5,751,125 to Weiss, which is incorporated herein by reference. The controller 76 could be used to operate the motor 52 in the manner disclosed in U.S. Pat. No. 5,751,125 to Weiss and/or U.S. Pat. No. 5,674,281 to Snyder, both of which patents are incorporated herein by reference. However, the particular manner in which the motor 52 is controlled is not considered important to the invention.

External and Internal Coils

The external coil network 108 may include an external coupler in the form of an electromagnetic transformer coil 150 (FIG. 4) and a capacitor 148 (FIG. 4) connected in series with the external coil 150. The internal coil network 130 may include an internal coupler in the form of an electromagnetic transformer coil 152 (FIG. 6) and a capacitor 154 connected in series.

Figure 2:
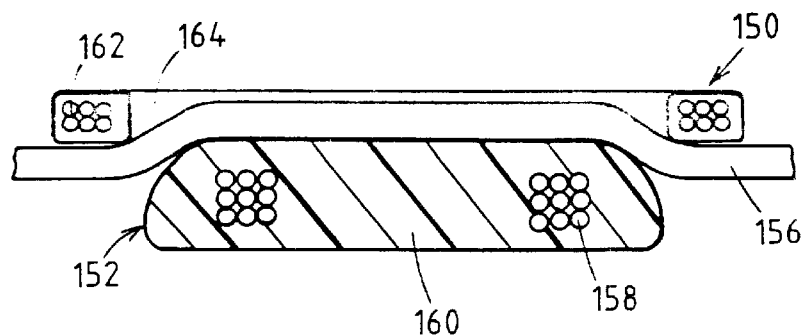
FIG. 2 is a cross-sectional side view of a pair of coils used in connection with an embodiment of the invention.

Referring to FIG. 2, the internal coil 152 is disposed beneath the skin 156 of a subject, and the external coil 150 is disposed generally adjacent the internal coil 152. The internal coil 152 may have a plurality of conductive windings 158 disposed in a circular insulating member 160, and the external coil 150 may have a plurality of conductive windings 162 disposed in an insulating ring 164. As is known, the inductance of each of the coils 150, 152 is determined by the number, diameter and spacing of the windings 158, 162. The inductive or electromagnetic coupling between the coils 150, 152 is a function of their physical proximity, their operating frequency, and their inductances. Coils of other shapes and structures could be used.

The coils 150, 152 together constitute a loosely coupled transformer, with the external coil 150 acting as a primary winding and the internal coil 152 acting as a secondary winding. The coils 150, 152 and the capacitors 148, 154 with which they may be connected may form a resonant circuit. The coils 150, 152 may be tuned to the same, or different, resonant frequencies. For example, the coils 150, 152 may be series tuned to a power transmission frequency of about 200 kHz.

The external coil 150 may induce an electric current in the internal coil 152, and the internal coil 152 may induce an electric current in the external coil 152, in accordance with the following equations:

$$I_{EXT}=V_{INT}(2\pi fk\sqrt{L_{EXT}L_{INT}}) \quad [1]$$

$$I_{INT}=V_{EXT}(2\pi fk\sqrt{L_{EXT}L_{INT}}) \quad [2]$$

where $I_{EXT}$ is the current induced in the external coil network 108, where $I_{INT}$ is the current induced in the internal coil network 130, where $V_{EXT}$ is the voltage across the external coil network 108, where $V_{INT}$ is the voltage across the internal coil network 130, where f is the frequency of the voltage across the coils 150, 152, where $L_{EXT}$ is the inductance of the external coil 150, where $L_{INT}$ is the inductance of the internal coil 152, where k is a constant, and where the coil networks are tuned to the same frequency f.

DC-to-AC Converter 104

Figure 4:
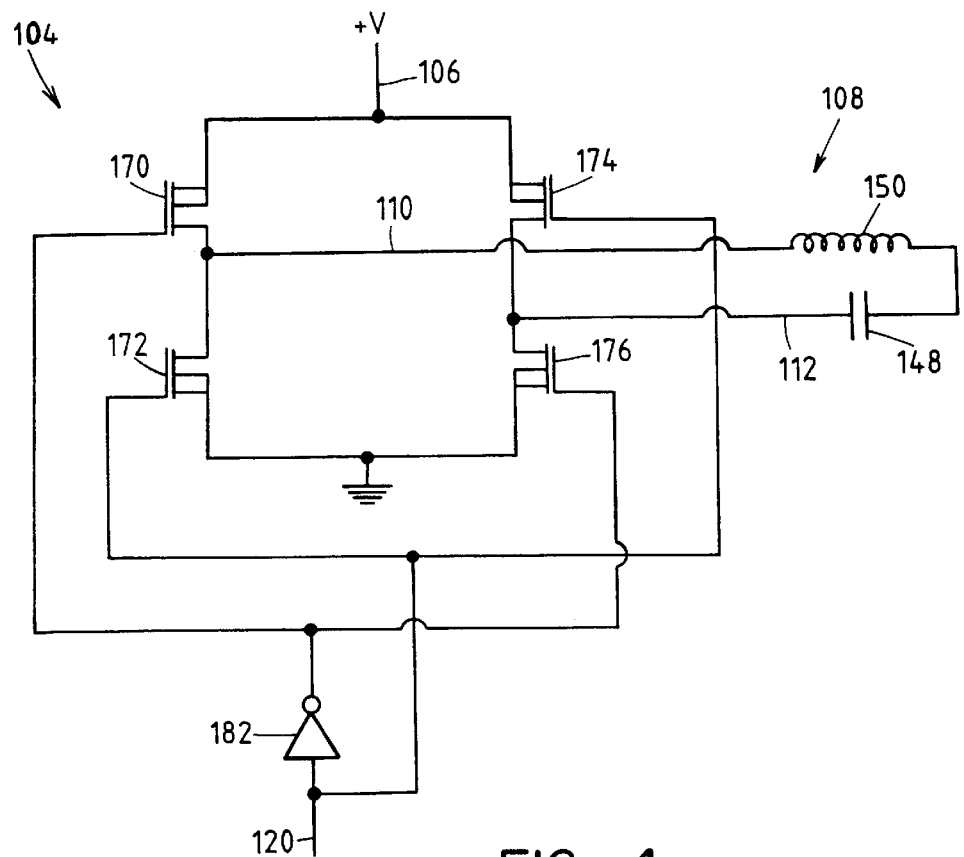
FIG. 4 is a circuit diagram of a DC-to-AC converter shown schematically in FIG. 3.

FIG. 4 is a circuit diagram of the DC-to-AC converter 104 shown schematically in FIG. 3 and also shows the external coil network 108. Referring to FIG. 4, the DC-to-AC converter 104 may comprise four transistors 170, 172, 174, 176, which may be metal oxide field-effect transistors (MOSFETs), connected in an H-bridge configuration. Each of the transistors 170, 172, 174, 176 is controlled by a respective high-frequency drive signal provided on the conductor 120, with two of the drive signals being 180° out of phase, or complemented, with respect to the other two via an inverter 182. The drive signals may be 50% duty cycle square waves provided at a frequency of about 200 kHz, for example. Although a particular type of DC-to-AC converter has been described above, any type of electronic switching network that generates a high-frequency voltage may be used.

Power Circuit 132a

Figure 6:
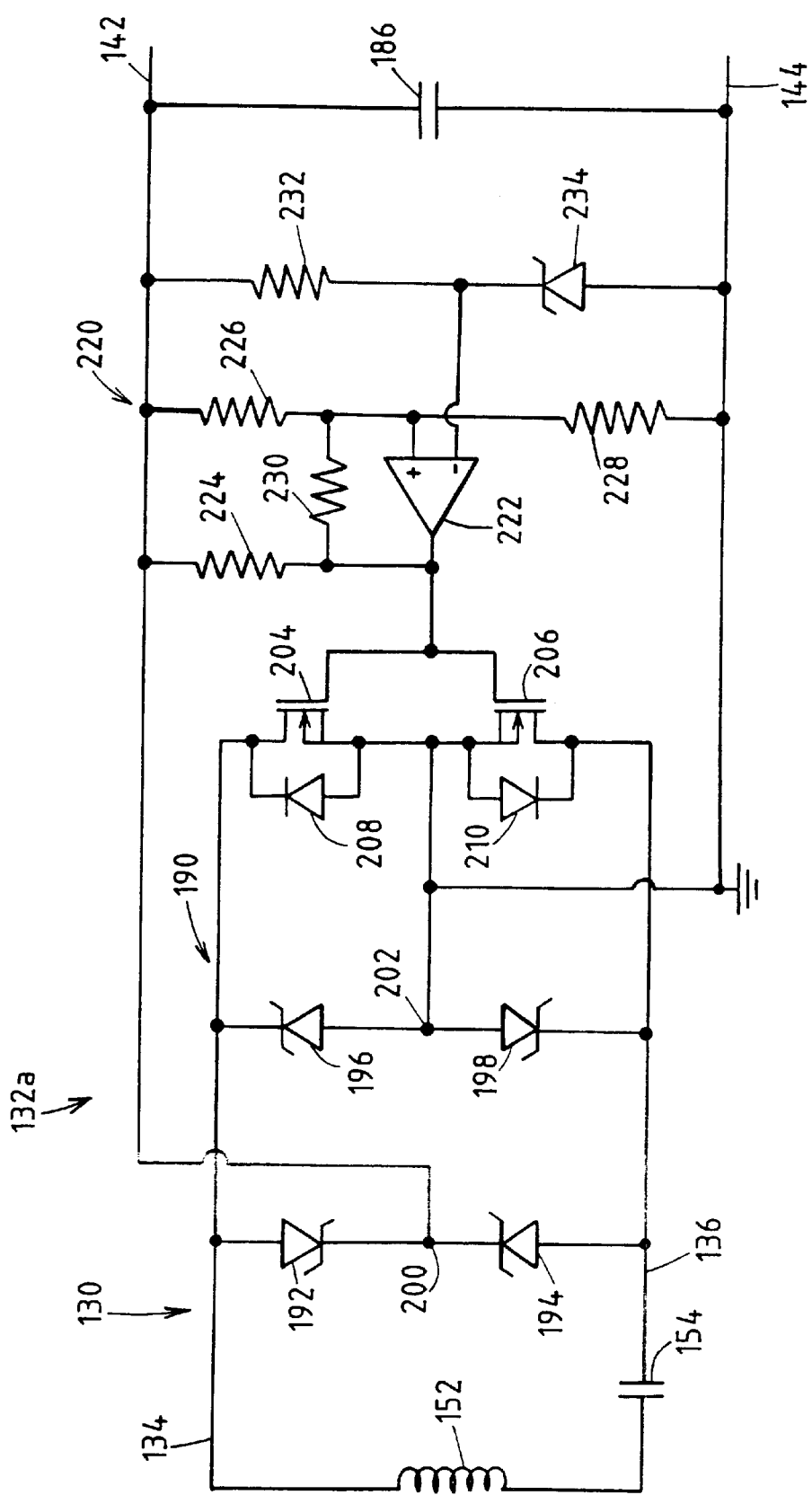
FIG. 6 is a circuit diagram of a first embodiment of the power circuit shown schematically in FIG. 3.

FIG. 6 illustrates the internal coil network 30 shown schematically in FIG. 3 and a power circuit 132a, which is one possible embodiment of the power circuit 132 schematically shown in FIG. 3. Referring to FIG. 6, the power supply circuit 132a acts as a voltage regulator to regulate the voltage stored by a relatively large, power supply capacitor 186. The voltage across the capacitor 186 is output via the lines 142, 144 to the controller 76 (FIG. 3) and to the pump 29 which includes the pump motor 52.

The power circuit 132a includes an AC-to-DC converter 190 that performs full wave rectification of the sinusoidal AC current induced in the internal coil 152 by the external coil 150. The AC-to-DC converter 190 may include four switching elements, which may be provided in the form of diodes or Schottky diodes 192, 194, 196, 198. The conductor 142 is connected to the intersection 200 of the diodes 192, 194 and carries a relatively high output voltage, and the conductor 144 is connected to the intersection 202 of the diodes 196, 198 and is grounded.

A switching transistor 204 is connected in parallel with the diode 196, and a switching transistor 206 is connected in parallel with the diode 198. The switching transistors 204, 206 may be field-effect transistors, and they may have a pair of diodes 208, 210 integrally formed therewith.

A switching control circuit 220 may be provided to control the conductive state of the transistors 204, 206. The switching control circuit 220 may be provided with a comparator 222, a plurality of biasing resistors 224, 226, 228, a feedback resistor 230, and a threshold setting circuit, which may be in the form of a resistor 232 and a Zener diode 234.

Operation of Power Circuit 132a

During operation, the motor 52 drives the pusher plates 30, 50 in a reciprocal fashion to pump blood through the artificial heart assembly 10 as described above, drawing electric current from the power supply capacitor 186. As current is drawn from the capacitor 186, the voltage across the capacitor 186 will decrease.

To replenish the voltage on the capacitor 186, the power circuit 132a may periodically operate in a power supply mode in which electric current generated by the AC-to-DC converter 190 is provided to the capacitor 186 via the line 142. When not operating in the power supply mode, the power circuit 132 operates in an idle mode in which current is not supplied to the capacitor 186.

Whether the power circuit 132a operates in the power supply mode or in the idle mode may be controlled based on the magnitude of the output voltage across the power supply capacitor 186. For example, if the output voltage falls below a certain value, the power circuit 132a may operate in the power supply mode. When the output voltage rises to a certain value, the power supply circuit 132a may operate in the idle mode.

By selectively supplying current to the power supply capacitor 186 only during certain times (i.e. the power supply mode), the voltage across the capacitor 186 is regulated, or maintained within a predetermined voltage range, such as between about 13 and about 14 volts, for example.

FIG. 7A illustrates the magnitude of the voltage across the power supply capacitor 186, which is referred to as $V_{OUT}$, as it changes over time. Referring to FIG. 7A, $V_{OUT}$ gradually decreases (during the idle mode) as current is drawn from the capacitor 186, and gradually increases (during the power supply mode) when current is supplied to the capacitor 186 from the AC-to-DC converter 190.

Referring also to FIG. 6, whether the power circuit 132a is in the power supply mode or the idle mode is controlled by the comparator 222, which basically compares a sensing voltage $V_{SENSE}$ derived from $V_{OUT}$ with a predetermined threshold voltage $V_{REF}$. When $V_{SENSE}$ is greater than $V_{REF}$, the output voltage $V_{CONTROL}$ of the comparator 222 is high and the power circuit 132a is in the idle mode. When $V_{SENSE}$ is not greater than $V_{REF}$, the output voltage $V_{CONTROL}$ of the comparator 222 is low and the power circuit is in the power supply mode.

Referring to FIG. 6, the inverting input of the comparator 222 is connected to sense the voltage $V_{REF}$ at the intersection of the resistor 232 and the Zener diode 234, which is a fixed voltage due to the Zener diode 234. The noninverting input of the comparator 222 is connected to sense the voltage $V_{SENSE}$ at the intersection of the resistors 226, 228, which form a voltage divider of the output voltage on the power supply capacitor 186 since the resistors 226, 228 are in parallel with the capacitor 186.

The feedback resistor 230 may be used to provide hysteresis to ensure that the power supply mode lasts for a minimum duration. Referring to FIG. 7B, when the value of $V_{SENSE}$ drops below $V_{REF}$ causing $V_{CONTROL}$ to be a low voltage, the feedback resistor 230 causes the value of $V_{SENSE}$ to drop further as shown in FIG. 7B (the value of $V_{SENSE}$ drops because the resistor 230 is essentially in parallel with the resistor 228 when $V_{CONTROL}$ is a low voltage). And when the value of $V_{SENSE}$ increases to reach $V_{REF}$, causing $V_{CONTROL}$ to be a high voltage, the feedback resistor 230 causes the value of $V_{SENSE}$ to increase further as shown in FIG. 7B (the value of $V_{SENSE}$ increases because the resistor 230 is no longer essentially in parallel with the resistor 228).

The conductive state of the transistors 204, 206 (which may be N-channel MOSFETs) is controlled by $V_{CONTROL}$. When $V_{CONTROL}$ is a low voltage, meaning that the power circuit 132a is in the power supply mode, the transistors 204, 206 will both be turned off and will have a relatively high impedance and act essentially as open circuits. In that case, during one half-cycle, electric current will flow from electrical ground at the conductor 144, down through the diode 198, up through the internal coil 152, and down through the diode 192 to the conductor 142 where it is supplied to charge the power supply capacitor 186. During the next half-cycle, electric current will flow from electrical ground at the conductor 144, up through the diode 196, down through the internal coil 152, and up through the diode 194 to the conductor 142 where it is supplied to charge the power supply capacitor 186.

When $V_{CONTROL}$ is a high voltage, meaning that the power circuit 132a is in the idle mode, the transistors 204, 206 will both be turned on, have a relatively low impedance, and act essentially as short circuits to short out the diodes 196, 198 with which they are in parallel. In that case, electric current flowing upwards through the internal coil 152 during one half-cycle will bypass the diode 192 that leads to the conductor 142 and will flow through the transistor 204 to ground. Electric current flowing downwards through the internal coil 152 during the next half-cycle will bypass the diode 194 that leads to the conductor 142 and will flow through the transistor 206 to ground. Consequently, little or no electric current is supplied to charge the capacitor 186 during the idle mode.

Controller 116a

Figure 5:
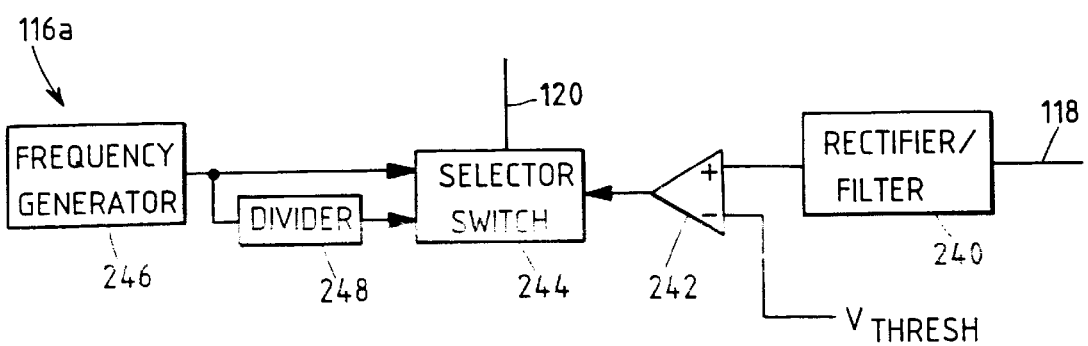
FIG. 5 is a block diagram of one embodiment of a controller shown schematically in FIG. 3.

FIG. 5 is a block diagram of a controller 116a, which is one embodiment of the controller 116 shown schematically in FIG. 3. The controller 116a changes the frequency at which the DC-to-AC converter 104 operates to conserve electric power during the idle mode described above. During the idle mode, when electric current is not being supplied to the capacitor 186, the power transmitted to the internal coil 152 by the external coil 150 is reduced in order to conserve the power of the DC power source 102 (FIG. 3), which may be a battery. This is accomplished by changing the frequency at which the DC-to-AC converter 104 operates.

As noted above, the internal and external coils 150, 152 may be tuned to a power transmission frequency, such as 200 kHz. Consequently, when it is desired to transmit power to the internal coil 152, the DC-to-AC converter 104 is operated at the power transmission frequency to which it is tuned. However, when it is not necessary to transmit a significant amount of power, such as during the idle mode above, the frequency of the DC-to-AC converter 104 is changed.

For example, the frequency at which the DC-to-AC converter 104 operates during the power-supply mode may be changed to an odd subharmonic of that frequency during the idle mode. For example, the idle mode frequency may be $\frac{1}{3}$, $\frac{1}{5}$, $\frac{1}{7}$, $\frac{1}{9}$ of the power supply mode frequency. The amount of power transmitted to the internal coil 152 varies with the idle mode frequency, with less power being transmitted at the seventh subharmonic (i.e. $\frac{1}{7}$ of the power supply mode frequency, or 28.6 kHz if the power transmission frequency is 200 kHz) and more power being transmitted at the third subharmonic (i.e. $\frac{1}{3}$ of the power supply mode frequency). Since odd subharmonics of a fundamental frequency still contain, in accordance with Fourier analysis, some components of the fundamental frequency, using an odd subharmonic of the power supply mode frequency during idle mode will still result in some power being transmitted to the internal coupler 152, which is generally desirable.

Referring to FIG. 5, the controller 116a has a rectifier/filter circuit 240 connected to the current sensor 114 (FIG. 3) via the line 118. The rectifier/filter circuit 240 generates a voltage that is provided to the noninverting input of a comparator 242, which has its inverting input connected to receive a fixed threshold voltage $V_{THRESH}$. The rectifier/filter circuit 240 and the comparator 242 act as an idle-mode-detection circuit to detect when the power circuit 132a is operating in the idle mode.

In particular, the rectifier/filter circuit 240 generates a voltage that is indicative of the magnitude of the electric current flowing through the external coil 150, which current is proportional to the voltage across the internal coil 152. During the idle mode, the transistors 204, 206 are turned on and present relatively small impedances. Since the transistors 204, 206 are connected essentially in parallel with the internal coil network 130, when they are turned on during the idle mode, the transistors 204, 206 cause the voltage across the internal coil network 130 to significantly decrease. That voltage decrease causes the current induced in the external coil 150 to be significantly decreased, in accordance with Equation [1] set forth above. Consequently, the voltage generated by the rectifier/filter circuit 240 decreases significantly when the power circuit 132a is in the idle mode. The comparator 242 detects that decrease when the voltage provided to its noninverting input falls below the threshold voltage $V_{THRESH}$ provided to its inverting input.

The output of the comparator 242 is connected to the select input of a frequency selector switch 244. The selector switch 244 has a first frequency input coupled to receive a drive signal having a first frequency, such as 200 kHz, generated by a frequency generator 246. The selector switch 246 has a second frequency input connected to receive a drive signal output from a frequency divider 248, that may generate a frequency that is an odd subharmonic of the frequency generated by the frequency generator 246.

When the power circuit 132a is in the power-supply mode as detected by the comparator 242, the selector switch 244 causes the drive signal generated by the frequency generator 246 to be supplied to the DC-to-AC converter 104 via the line 120. When the power circuit 132a is in the idle mode as detected by the comparator 242, the selector switch 244 causes the drive signal generated by the frequency divider 248 to be supplied to the DC-to-AC converter 104 via the line 120.

Power Circuit 132b

Figure 10:
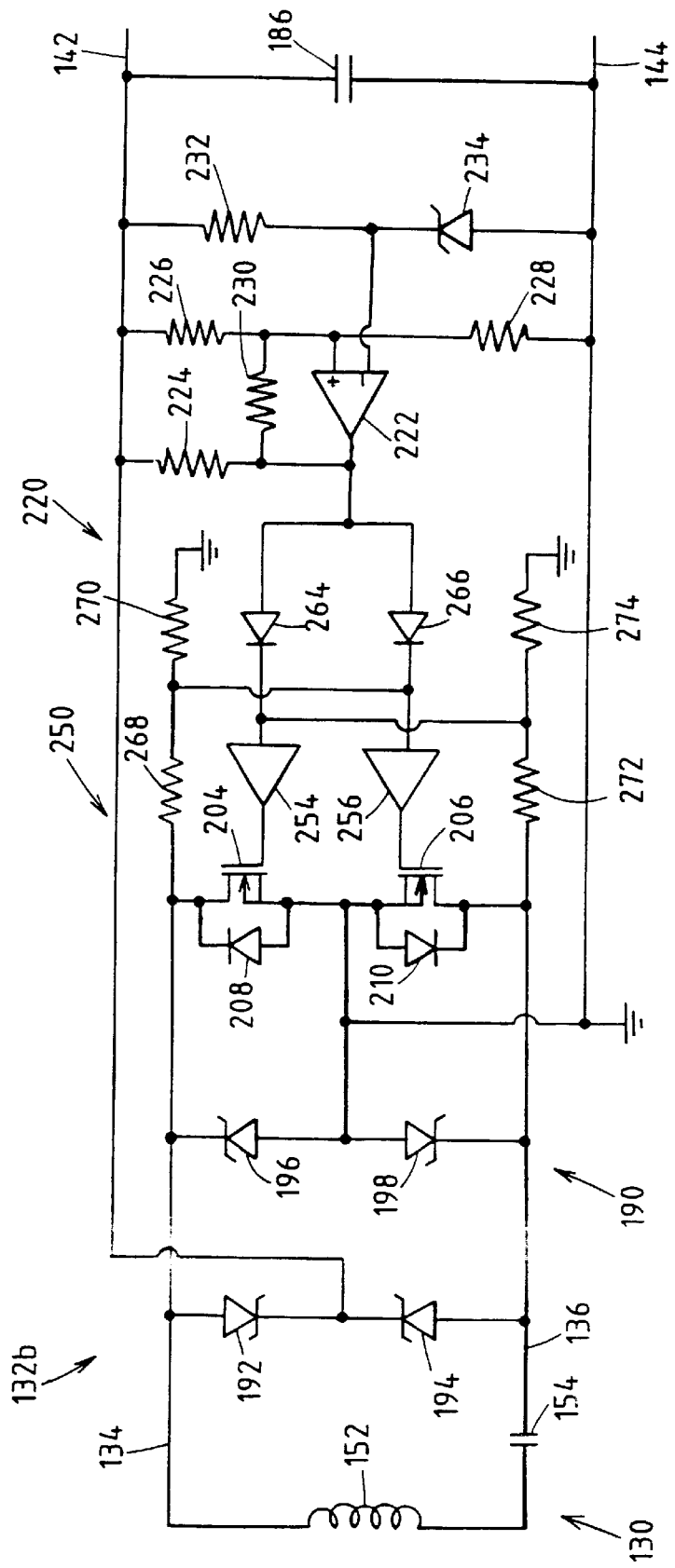
FIG. 10 is a circuit diagram of an alternative power circuit.

FIG. 10 illustrates the internal coil network 130 shown schematically in FIG. 3 and a power circuit 132b, which is one possible embodiment of the power circuit 132 schematically shown in FIG. 3. Referring to FIG. 10, the power circuit 132b is similar to the power circuit 132a shown in FIG. 6 and described above, except that a synchronous drive circuit 250 is included between the transistors 204, 206 and the comparator 222.

The synchronous drive circuit 250 may be provided in the form of a pair of driver circuits 254, 256, such as MOSFET drivers, a pair of diodes 264, 266 connected to the inputs of the driver circuits 254, 256, and four resistors 268, 270, 272, 274. As shown in FIG. 10, the intersection of the resistors 268, 270 is connected to the input of the driver circuit 256, and the intersection of the resistors 272, 274 is connected to the input of the driver circuit 254.

The idle mode of the power circuit 132b is substantially the same as the idle mode described above in connection with the power circuit 132a. During the idle mode of the power circuit 132b, the comparator 222 generates a relatively high voltage on its output. That high voltage causes the voltage at the output of each of the diodes 264, 266 to be high, which in turn causes the voltage output by the driver circuits 254, 256 to be high, which in turn causes both of the transistors 254, 256 to be turned on, so that no significant amount of electric current is provided to the power supply capacitor 186, as described above.

When the output of the comparator 222 is not high, so that the power circuit 132b is not in the idle mode, the transistors 204, 206 are switched on and off at a high rate that is synchronous with the voltage induced across the internal coil 152 by the external coil 150. At any point in time, exactly one of the transistors 204, 206 is turned on, with the other of the transistors 204, 206 being turned off.

The switching of the transistors 204, 206 during the power supply mode causes current to be supplied to the power supply capacitor 186 through the transistors 204, 206. In particular, during one half-cycle, electric current will flow from electrical ground at the conductor 144, down through the transistor 206, up through the internal coil 152, and down through the diode 192 to the conductor 142 where it is supplied to charge the power supply capacitor 186. During the next half-cycle, electric current will flow from electrical ground at the conductor 144, up through the transistor 204, down through the internal coil 152, and up through the diode 194 to the conductor 142 where it is supplied to charge the power supply capacitor 186.

It should be noted that, in the power circuit 132a, current flows through all four of the diodes 192, 194, 196, 198 during the power supply mode. However, as described above, in the power circuit 132b, current flows through only two of the diodes, i.e. diodes 192, 194, during the power supply mode. Instead of flowing through the diodes 196, 198 in the power circuit 132b, current flows through the transistors 204, 206. That saves electric power since the transistors 204, 206 have a lower voltage drop associated with them than the diodes 196, 198, which results in less power dissipation in the transistors 204, 206 as compared with the diodes 196, 198.

The switching control of the transistor 204 during the power supply mode is automatically controlled by the voltage $V_{204}$ at the intersection of the resistors 272, 274, and the switching control of the transistor 206 during the power supply mode is automatically controlled by the voltage $V_{206}$ at the intersection of the resistors 268, 270. The transistor 204 is turned on only when $V_{204}$ is a relatively high voltage, and the transistor 206 is turned on only when $V_{206}$ is a relatively high voltage.

When the diode 192 is turned on by current flow through it from the internal coil 152 during one half-cycle, the voltage $V_{206}$ is a relatively high voltage, since it is substantially equal to the output voltage across the capacitor 186 minus the voltage drop across the diode 192. In that case, the transistor 206 is turned on so that the current flows through the transistor 206, the internal coil 152, and the diode 192 as described above.

When the diode 194 is turned on by current flow through it from the internal coil 152 during the next half-cycle, the voltage $V_{204}$ is a relatively high voltage, since it is substantially equal to the output voltage across the capacitor 186 minus the voltage drop across the diode 194. In that case, the transistor 204 is turned on so that the current flows through the transistor 204, the internal coil 152, and the diode 194 as described above.

Modifications of the power circuit 132b shown in FIG. 10 could be made. For example, the diodes 196, 198 could be omitted from the circuit 132b. Alternatively, the diodes 192, 194, 196 and 198 could be omitted, and four transistors like the transistors 204, 206 (and diodes 208, 210) could be used in their place.

Power Circuit 132c

Figure 11:
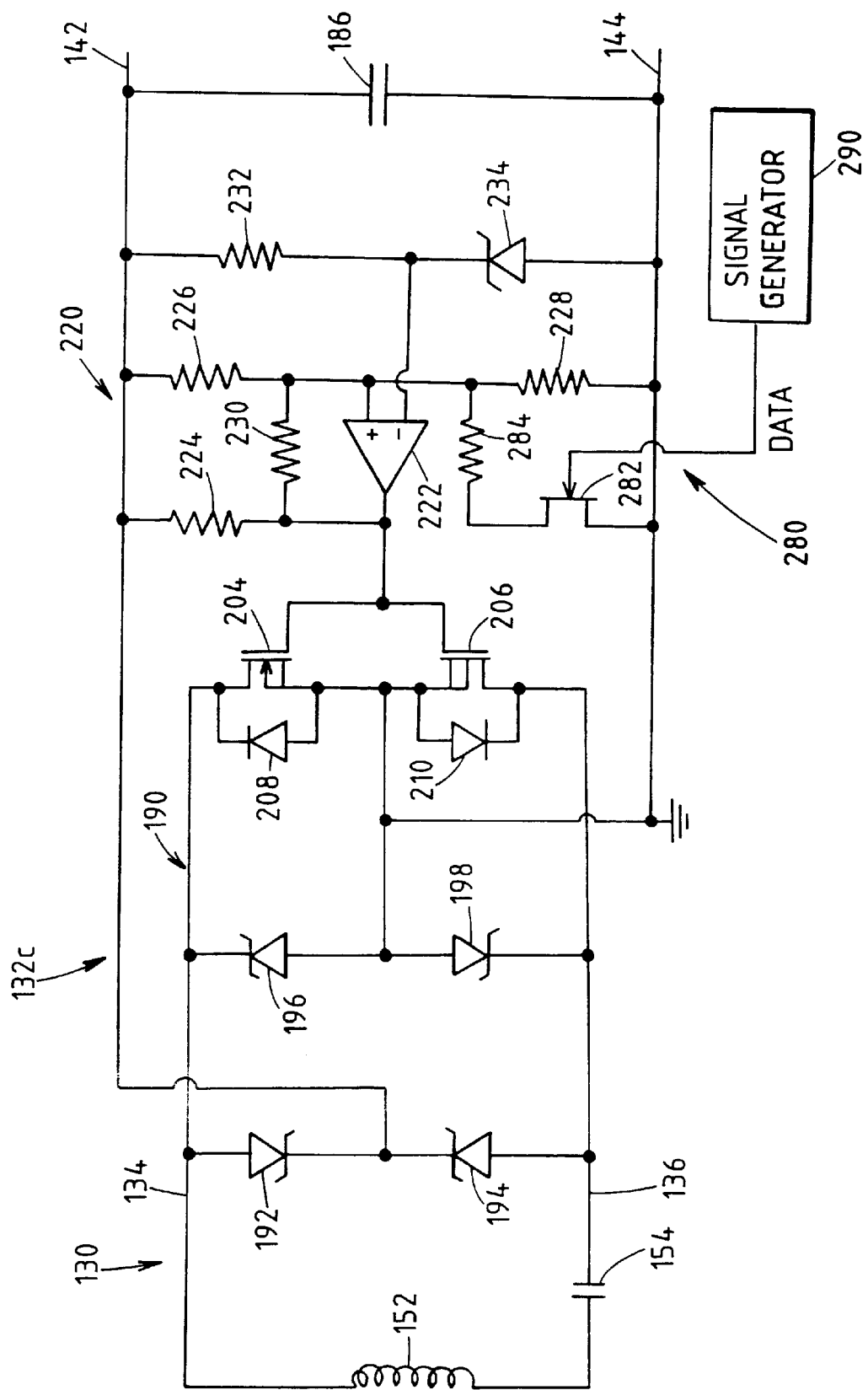
FIG. 11 is a circuit diagram of another embodiment of a power circuit.

FIG. 11 illustrates the internal coil network 30 shown schematically in FIG. 3 and a power circuit 132c, which is another possible embodiment of the power circuit 132 schematically shown in FIG. 3. Referring to FIG. 11, the power circuit 132c is similar to the power circuit 132a shown in FIG. 6 and described above, except that a voltage modulating circuit 280 is included.

The voltage modulating circuit 280 could be provided in the form of a switching transistor 282 and a resistor 284 connected in series, the combination of which is connected in parallel with the resistor 228. It should be noted that when the transistor 282 is turned on, via a data signal provided to its input, the resistor 284 is effectively in parallel with the resistor 228. It should be noted that the combined resistance of the parallel-connected resistors 228, 284 is lower than the resistance of the resistor 228 alone. Consequently, that lower combined resistance lowers the value of $V_{SENSE}$ (with respect to $V_{OUT}$) provided to the noninverting input of the comparator 222, which is used to control the voltage limits on the power supply capacitor 186, as described above. The reduction of $V_{SENSE}$ will thus result in a higher output voltage across the capacitor 186. The data signal provided to the transistor 282 may be generated by a signal generator 290, which may be a computer or controller programmed with appropriate software, for example, or another type of signal generator.

FIG. 8 illustrates how the output voltage $V_{OUT}$ across the power supply capacitor 186 may change in response to the switching of the transistor 282. Referring to FIG. 8, $V_{OUT}$ is shown to vary between a variable upper limit or envelope 292 and a variable lower limit or envelope 294. The upper envelope 292 may have a relatively high value during each period of time during which the transistor 282 is switched on, and the upper envelope signal 292 may have a relatively low value during each period of time during which the transistor 282 is switched off. Similarly, the lower envelope 294 may have a relatively high value during each period of time during which the transistor 282 is switched on, and the lower envelope signal 294 may have a relatively low value during each period of time during which the transistor 282 is switched off.

It should be noted that the magnitude changes of the upper and lower envelopes 292, 294 coincide with the magnitude changes of the data signal, noted above, used to control the transistor 282. FIG. 9A illustrates a data signal 296 that, when provided to control the transistor 282, would result in the output voltage $V_{OUT}$ having the envelopes 292, 294. The data signal 296 has portions with a relatively high magnitude that may be used to represent logic "1" and portions with a relatively low magnitude that may be used to represent logic "0," as shown in FIG. 9A. The data signal 296 could be used as a transmit data signal in order to transmit desired data; which may be represented by various combinations of logic "1" and logic "0."

Alternatively, other methods of data encoding could be used. For example, instead of a logic "1" being represented by a relatively large magnitude and a logic "0" being represented by a relatively small magnitude, a data signal could be utilized in which logic "1" is represented by a high-frequency portion of the data signal and in which logic "0" is represented by a low-frequency portion of the data signal, as shown in FIG. 9B by a data signal 298.

Referring to FIG. 8, it should be noted that the frequency of the envelopes 292, 294 is lower than the frequency at which the output voltage $V_{OUT}$ changes. It should also be understood that the rate at which $V_{OUT}$ changes in magnitude, and thus its frequency, depends on the rate at which the motor 52, or other component (s), draw electric current from the power supply capacitor 186.

Alternative Embodiment of External Assembly 90

Figure 12:
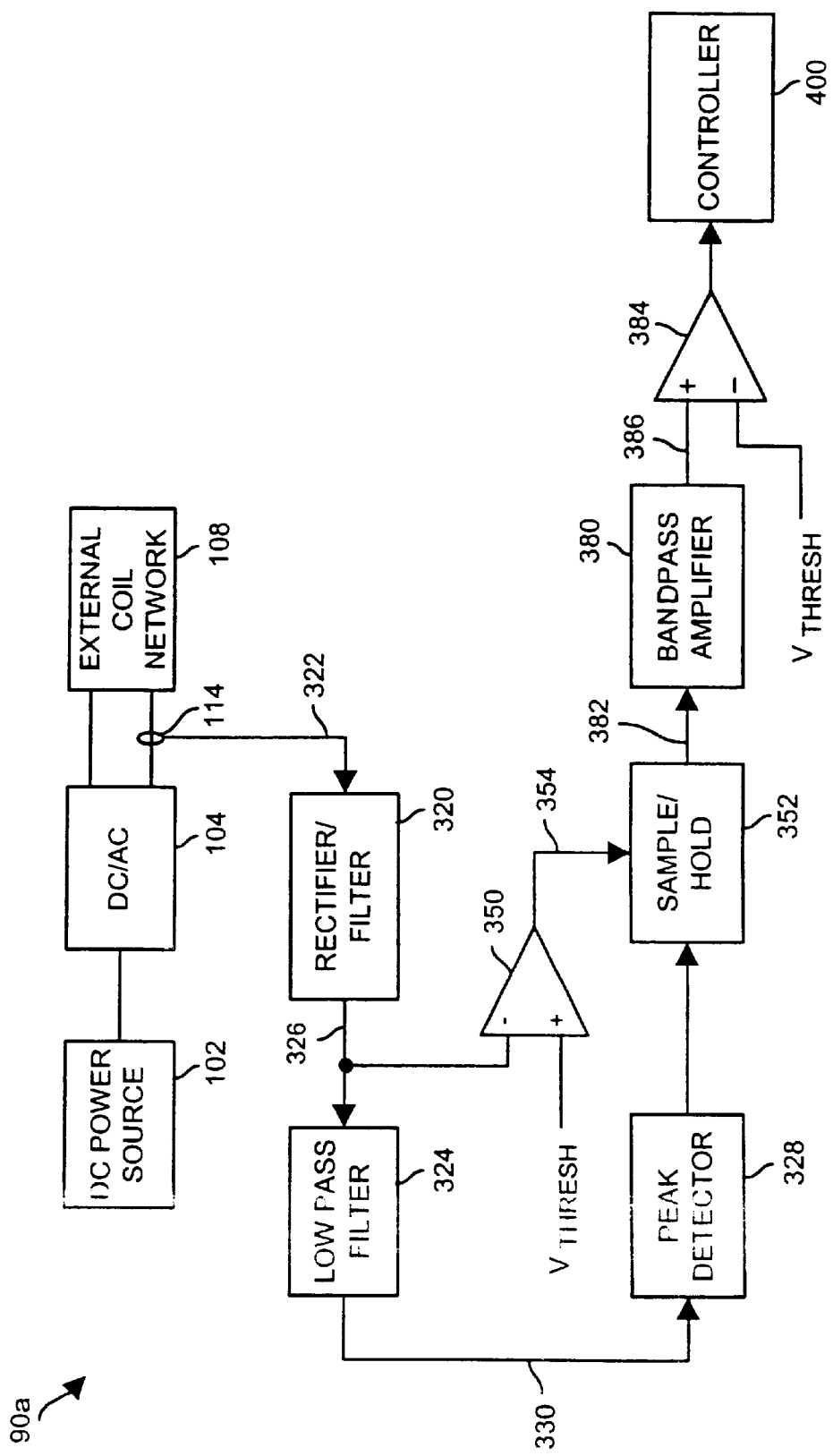
FIG. 12 is an alternative embodiment of an external assembly.

FIG. 12 is a block diagram of an external assembly 90a, which is another possible embodiment of the external assembly 90 schematically shown in FIG. 3. The external assembly 90a is used to recover and decode data from electric power transmitted between the internal coil 152 and the external coil 150.

Referring to FIG. 12, the external assembly 90a may include the same DC power source 102, the DC-to-AC converter 104, the external coil network 108 and current sensor 114 described above in connection with FIG. 3. The external assembly 90a includes other components designed to generate a data signal from the magnitude of the current that is induced in the external coil 150 by the voltage in the internal coil 152.

Figure 13A:
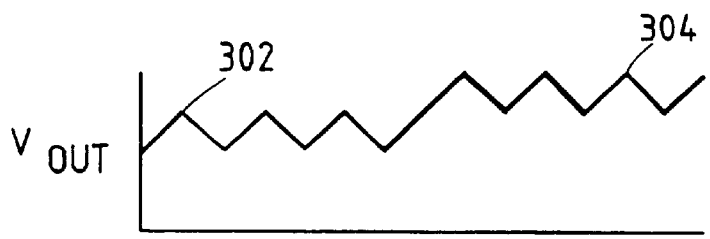
FIGS. 13A–13G illustrate various waveforms in connection with a data transmission method.

Referring to FIG. 13A, an exemplary graph of the voltage $V_{OUT}$ on the power supply capacitor 186 is shown to have three peaks 302 having relatively small magnitudes and three peaks 304 having relatively large magnitudes. Those peaks of different magnitudes may be produced by the voltage modulating circuit 280 described above and may represent different data values as described above in connection with FIGS. 8 and 9A.

Figure 13B:
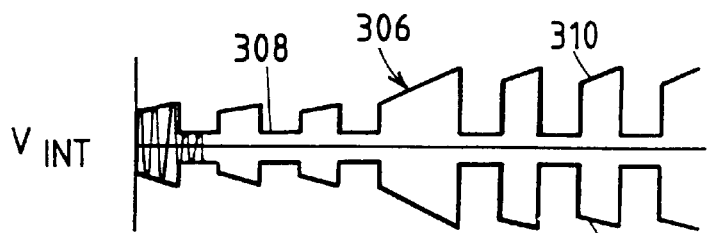

FIG. 13B illustrates a bipolar envelope waveform 306 of the relatively high-frequency, bipolar voltage $V_{INT}$ across the internal coil 152 that would correspond to the voltage $V_{OUT}$ shown in FIG. 13A. The envelope waveform 306 has relatively small positive and negative magnitudes 308 when the magnitude of $V_{OUT}$ is decreasing and relatively large positive and negative magnitudes 310 when the magnitude of $V_{OUT}$ is increasing.

Figure 13C:
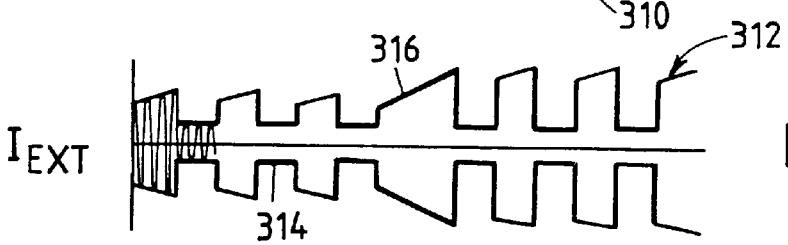

FIG. 13C illustrates a bipolar envelope waveform 312 of the relatively high-frequency, bipolar current $I_{EXT}$ that would be induced in the external coil 150 in response to the voltage $V_{INT}$ shown in FIG. 13B. The envelope waveform 312 is similar in the envelope waveform 306 and has relatively small positive and negative magnitudes 314 when the magnitude of $V_{OUT}$ is decreasing and relatively large positive and negative magnitudes 316 when the magnitude of $V_{OUT}$ is increasing.

Figure 13D:
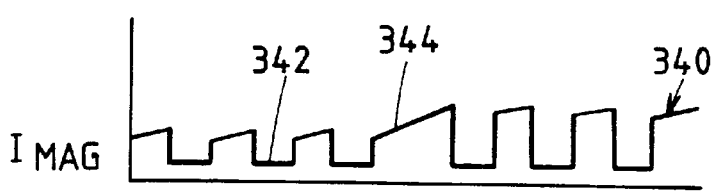

Referring to FIG. 12, the current sensor 114 may be provided to detect the relatively high-frequency current $I_{EXT}$, such as shown in FIG. 13C, passing through the external coil 150. A signal representative of the current $I_{EXT}$ may be provided to a rectifier/filter circuit 320 via a conductor 322, to a low-pass filter circuit 324 via a conductor 326, and to a peak detector 328 via a conductor 330. Referring also to FIG. 13D, the rectifier/filter circuit 320 could be used to generate a magnitude signal $I_{MAG}$ 340 (which is actually a voltage) on the conductor 326, with the $I_{MAG}$ signal having relatively small magnitude portions 342 when $I_{EXT}$ has relatively small magnitudes and having relatively large magnitude portions 344 when $I_{EXT}$ has relatively large magnitudes.

Referring to FIGS. 13A–13D, it should be noted that the $V_{INT}$, $I_{EXT}$ and $I_{MAG}$ waveforms have three trapezoidally shaped portions with a relatively small magnitude, which correspond to the peaks 302 of the $V_{OUT}$ waveform, and three trapezoidally shaped portions with a relatively large magnitude, which correspond to the peaks 304 of the $V_{OUT}$ waveform.

Referring also to FIG. 12, the $I_{MAG}$ signal 340 may be provided to a comparator 350 having an inverting input coupled to the conductor 326 and a noninverting input coupled to a threshold voltage $V_{THRESH}$. The comparator 350 may be used to control a sample and hold circuit 352, which samples and stores the peak values $I_{PEAK}$ of the $I_{MAG}$ signal, via a conductor 354.

Figure 13E:
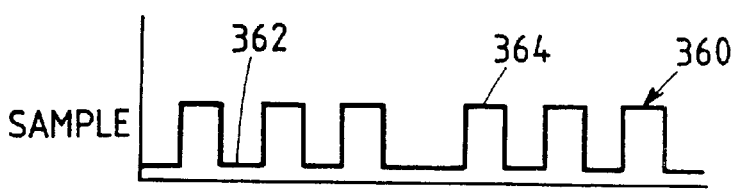

The comparator 350 may generate a control signal SAMPLE 360 (FIG. 13E) having relatively small magnitude portions 362 when the value of $I_{MAG}$ is larger than $V_{THRESH}$ and relatively large magnitude portions 364 when the value of $I_{MAG}$ is smaller than $V_{THRESH}$.

Figure 13F:
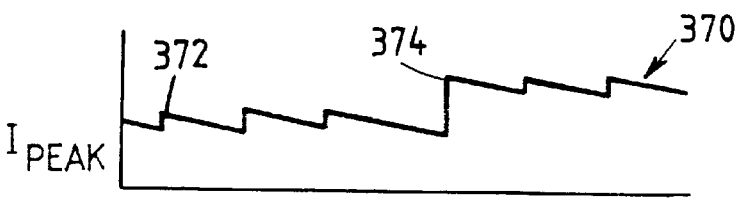

The sample and hold circuit 352 may be triggered on the rising edge of the SAMPLE signal so that the circuit 352 samples and stores voltages representing the peak values of the $I_{MAG}$ signal. A waveform $I_{PEAK}$ 370 representing such peak voltage values is shown in FIG. 13F. The $I_{PEAK}$ waveform 370 is shown to have three peaks 372 with relatively small magnitudes (and which correspond to the peaks 302 of $V_{OUT}$ shown in FIG. 13A) and three peaks 374 with relatively large magnitudes (and which correspond to the peaks 304 of $V_{OUT}$ shown in FIG. 13A).

Figure 13G:
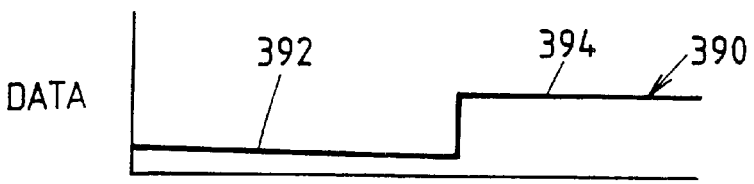

The output of the sample and hold circuit 352 may be provided to bandpass amplifier 380 for further signal processing via a line 382, and then to the noninverting input of a comparator 384 via a line 386. A threshold voltage $V_{THRESH}$ may be provided to the inverting input of the comparator 384 in order to generate a DATA signal 390 (FIG. 13G) having relatively low magnitudes 392 when the magnitude of the $I_{PEAK}$ signal 370 does not exceed the $V_{THRESH}$ voltage supplied to the comparator 384 and having relatively high magnitudes 394 when the magnitude of the $I_{PEAK}$ signal 370 exceeds the $V_{THRESH}$ voltage supplied to the comparator 384. The DATA signal 390 may be provided to a controller 400 for further processing or other purposes.

Referring to FIG. 20, the controller 400 could comprise various hardware components, including a random-access memory (RAM) 401, a program memory 402, such as a read-only memory (ROM) for storing a computer program, a microprocessor 403, an input/output (I/O) circuit 404, all of which are interconnected by an address/data bus 405. Other types of controllers could be utilized.

Although a particular decoding circuit for recovering data from the power transmitted from the internal coil 152 to the external coil 150 is described above, other decoding circuits could be utilized.

Frequency Detection

The data transmitted by modulating the voltage across the power supply capacitor 186 as described above could be frequency modulated in order to transmit data regarding the operation of the artificial heart assembly 10. For example, in order to communicate a fault condition from the internal assembly 100 to the external assembly 90, the voltage across the power supply capacitor 186 could be modulated so that the data signal 390 shown in FIG. 13G has a first frequency, such as 50 Hz, and in order to communicate that the internal assembly 100 is functioning properly, the voltage across the power supply capacitor 186 could be modulated so that the data signal 390 shown in FIG. 13G has a second frequency, such as 100 Hz. Additional frequencies could be used to communicate other conditions of the internal assembly 100.

Figure 14:
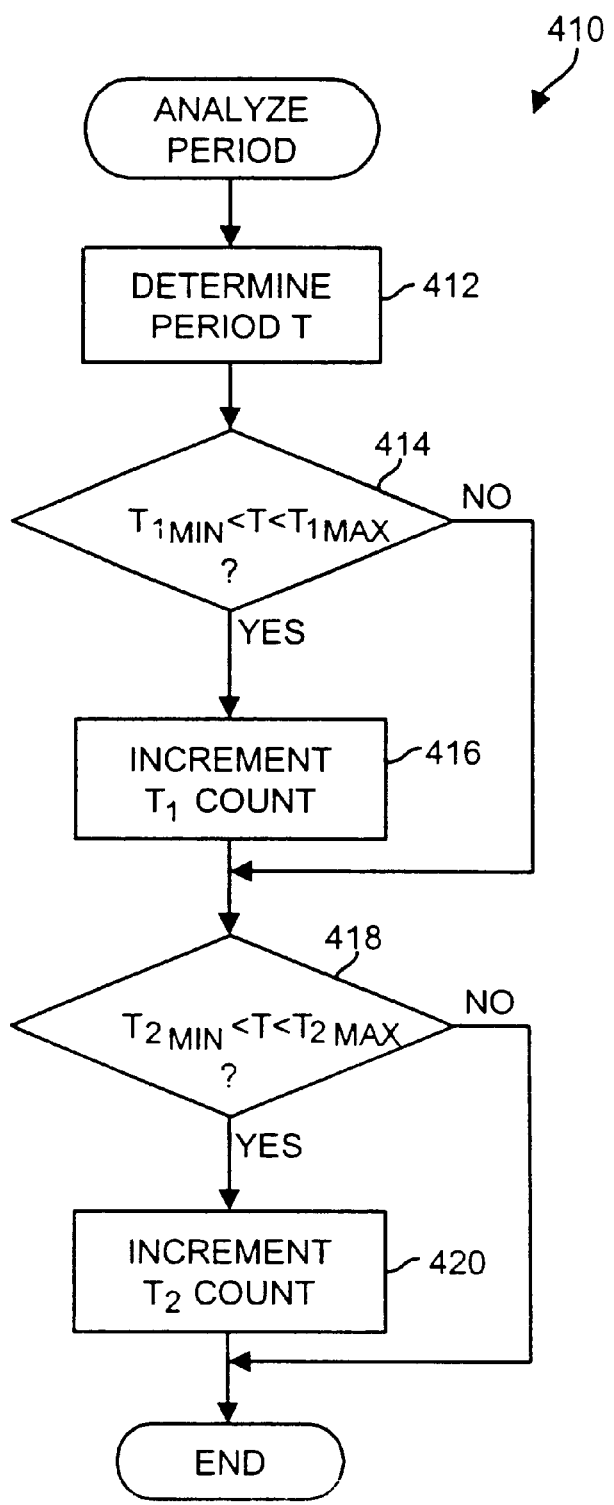
FIGS. 14 and 15 are flowcharts of software routines that may be used in connection with the data transmission method.
Figure 15:
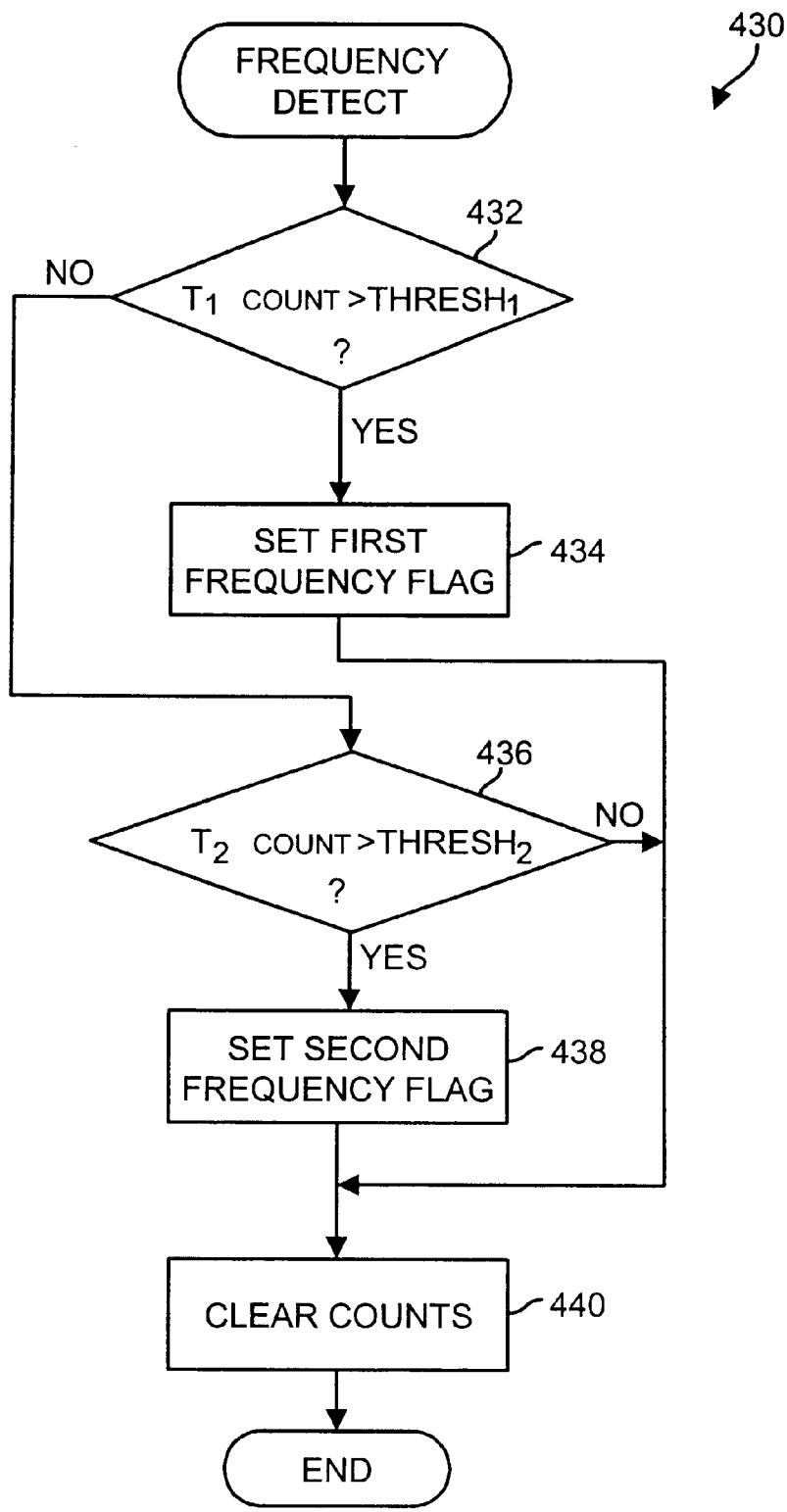

FIGS. 14 and 15 are flowcharts of a pair of computer program routines 410, 430 that could be performed by the controller 400 (FIG. 12) to determine frequency of the data signal 390. The computer program routines 410, 430 could be stored in memory, such as in the program memory 402 shown in FIG. 20. The purpose of the analyze period routine 410 shown in FIG. 14 is to measure the periods of the data signal 390 shown in FIG. 13G and to determine whether portions of the data signal 390 correspond to one of a number of predetermined signal frequencies that may be used to communicate various messages or conditions of the internal assembly 100. The analyze period routine 410 may be an interrupt service routine that is performed once for each detected cycle of the data signal 390, such as upon each rising edge of the data signal 390.

Referring to FIG. 14, at block 412, the period T of the most recently detected cycle of the data signal 390 is determined. The period may be determined, for example, by starting a clock or timer (not shown) upon detection of one rising edge of the data signal 390, and stopping the clock or timer upon detection of the next rising edge of the data signal 390.

At block 414, the routine determines whether the measured period T corresponds to a frequency that is one of the predetermined signalling frequencies. If not, the change in the data signal 390 could simply have been caused by electrical noise or other interference. At block 414, the time duration of the period T is compared with a minimum period duration $T1_{MIN}$ and a maximum period duration $T1_{MAX}$. For example, if a data signal having a frequency of 100 Hz is being detected, $T1_{MIN}$ could be set to eight milliseconds and $T1_{MAX}$ could be set to 12 milliseconds since a 100 Hz frequency signal should have cycles with periods of 10 milliseconds.

If the time duration of the period T is between the upper and lower values, then it is assumed that that cycle of the data signal 390 is of the signalling frequency corresponding to the period T1, and the routine branches to block 416 where a count ("T1 COUNT") of the number of detected cycles of that frequency is incremented by one.

Blocks 418 and 420 may be performed to detect another signalling frequency, such as 50 Hz (for which the corresponding period is 20 milliseconds in duration), by determining whether the current cycle of the data signal 390 has a period T that is between a minimum period $T2_{MAX}$, such as 16 milliseconds, and a maximum period $T2_{MAX}$, such as 24 milliseconds. Although the routine 410 of FIG. 14 is shown to check for the presence of two signalling frequencies, the routine 410 could test for any number of signalling frequencies.

The frequency detect routine 430 of FIG. 15 is performed less frequently than the routine 410 of FIG. 14, such as once every 10 or 20 times the routine 410 is performed, or alternatively, on a periodic basis such as once every second. The purpose of the routine 430 is to determine whether the data signal 390 corresponds to one of the signalling frequencies. In that case, it would be expected that all or a high percentage of the periods T previously measured by the analyze period routine 410 would have corresponded to the expected periods for that signalling frequency.

For example, assume that the data signal 390 is being transmitted at a 100 Hz signalling frequency (in which case $T1_{MIN}$ might be eight milliseconds and $T2_{MAX}$ might be 12 milliseconds), and that the frequency detect routine 430 is performed once every second. In that case, if the signal 390 were a perfect 100 Hz signal, the value of T1 COUNT would be 100 since 100 periods T within the expected period range would have been detected. However, since the data signal 390 may be corrupted by noise, a lower threshold number may be used. For example, if only 80 periods T within the period limits $T1_{MIN}$ and $T1_{MAX}$ are detected (as indicated by the value of T1 COUNT), the signal 390 will be recognized as a valid 100 Hz signalling frequency.

The above determination is carried out by the frequency detect routine 430 as follows. At block 432, the value of T1 COUNT is compared with a predetermined number THRESH1. If the value of T1 COUNT is larger than THRESH1, it is assumed that the data signal 390 is a valid signalling frequency, and the routine branches to block 434 where a first frequency flag is set to indicate such assumption. Other actions may also be performed in that case, such as the display of a message or the generation of an audible signal by the external assembly 90. Blocks 436 and 438 are performed to test for the presence of a second signalling frequency. At block 440, the values of T1 COUNT and T2 COUNT are reset to zero.

Energy-Recovery Mode

Figure 18A:
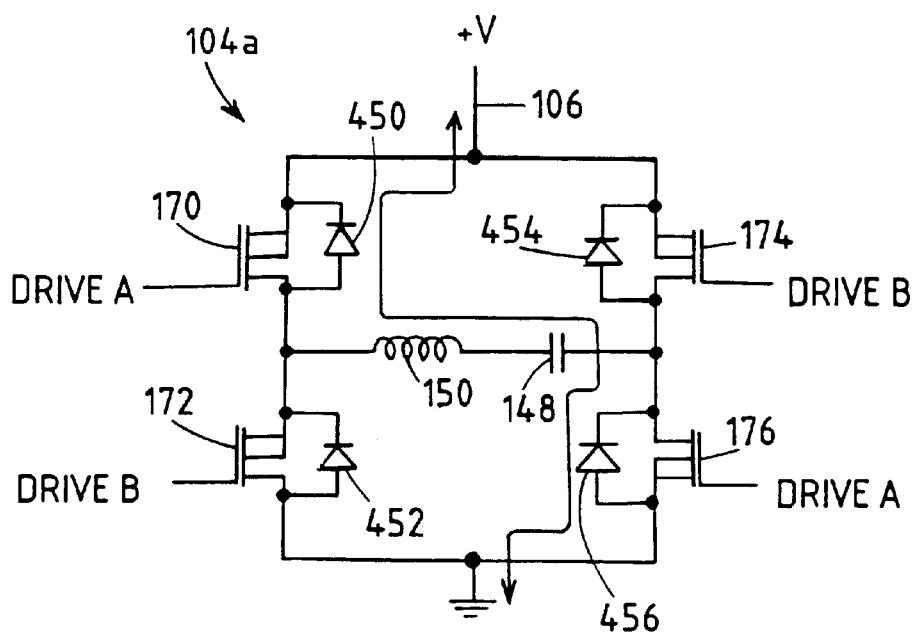
FIGS. 18A and 18B illustrate current flows through the AC-to-DC converter shown in FIG. 16.
Figure 18B:
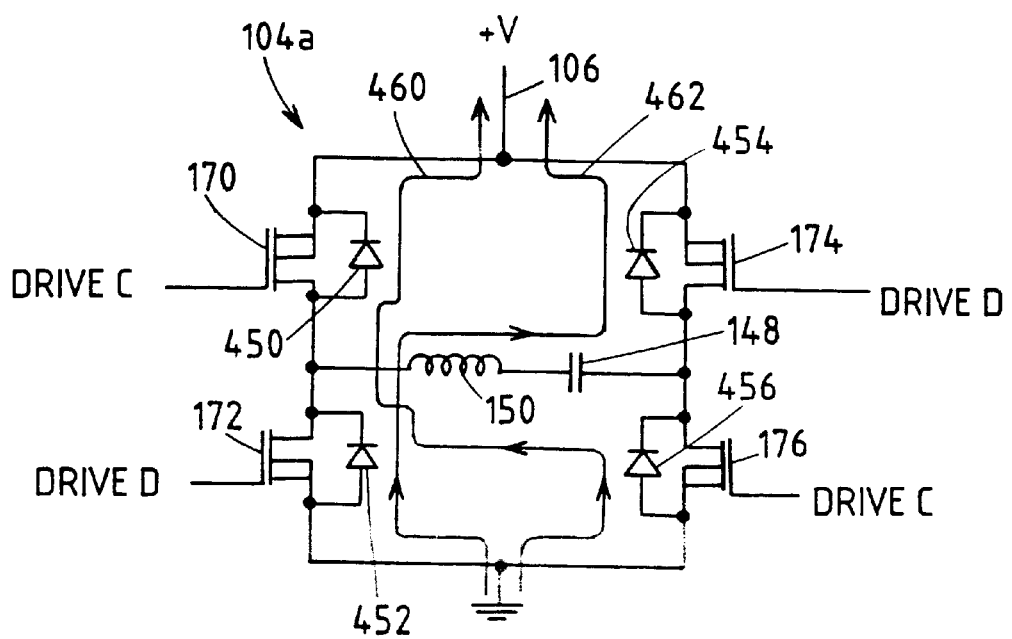

An alternative embodiment of a DC-to-AC converter 104a is shown in FIGS. 18A and 18B. The DC-to-AC converter 104a includes four diodes 450, 452, 454, 456, each of which is connected in parallel with one of the transistors 170, 172, 174, 176. The diodes 450, 452, 454, 456 may be integrally formed with the transistors 170, 172, 174, 176 on the same piece of semiconductive material.

Figure 16A:
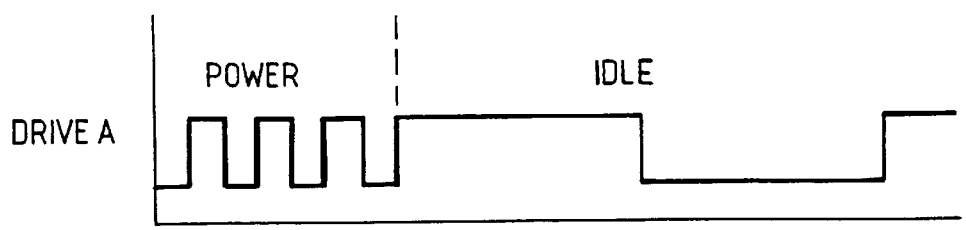
FIGS. 16A and 16B illustrate a set of waveforms for driving a DC-to-AC converter at one frequency during a power-supply mode and at a second frequency during an idle mode.
Figure 16B:
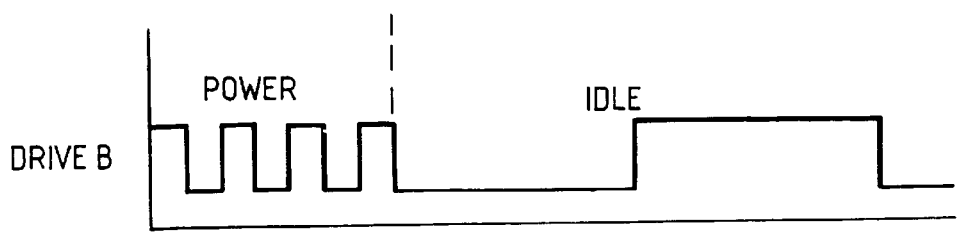

The artificial heart assembly 10 may be operated in a power-supply mode in which the DC-to-AC converter 104a is driven at a relatively high frequency, such as 200 kHz, and in an idle mode in which the DC-to-AC converter 104a is driven at a relatively low frequency, such as about 28 kHz. FIGS. 16A and 16B illustrate a pair of drive signals that may be used to drive the DC-to-AC converter 104a in such a fashion.

When the system switches from the power mode to the idle mode, the currents in the coils 150, 152 change from a high level to a low level. Due to the resonant properties of the loosely coupled coil networks 108, 130, this change in current takes a decay time that lasts many times longer than the period of the resonant frequency of the coil networks. During that decay time, alternating current continues to flow in the coils 150, 152 at the resonant frequency, which is referred to as "ringing." That energy is normally dissipated as heat in the coils 150, 152 and other circuit components.

The ringing described above will occur when two of the transistors 170–176 are on and when two of them are off, as indicated by the DRIVE A and DRIVE B signals shown in FIGS. 16A and 16B. Referring to FIGS. 16A and 18A, assume that the DRIVE A signal of FIG. 16A is connected to drive the transistors 170, 176 and that the DRIVE B signal is connected to drive the transistors 172, 174. When the circuit 104a transitions from the power mode to the idle mode, the transistors 170, 176 will be turned on for a relatively long period of time, during which they will essentially act as short circuits, and the transistors 172, 174 will be turned off for a relatively long period of time, during which they will essentially act as open circuits.

Consequently, when the circuit 104a transitions to the idle mode, during one half-cycle of the bidirectional ringing current, current will flow from electrical ground, through the transistor 176, through the capacitor 148 and the external coil 150, through the transistor 170, to the DC power source 102 (which is shown in FIG. 2 and represented by +V in FIGS. 18A and 18B), as indicated by the bidirectional arrow shown in FIG. 18A. During the next half-cycle of the ringing current, current will flow through those same components, but in the opposite direction. During the ringing noted above, electrical power will be wasted due to dissipation through the components of the circuit 104a.

In order to conserve electric power, the circuit 104a may be operated in an energy-recovery mode before the idle mode begins. During the energy-recovery mode, instead of turning two of the transistors 170–176 on and two of the transistors 170–176 off in accordance with the lower switching frequency, all four of the transistors 170–176 are simultaneously turned off for a period of time.

Figure 17A:
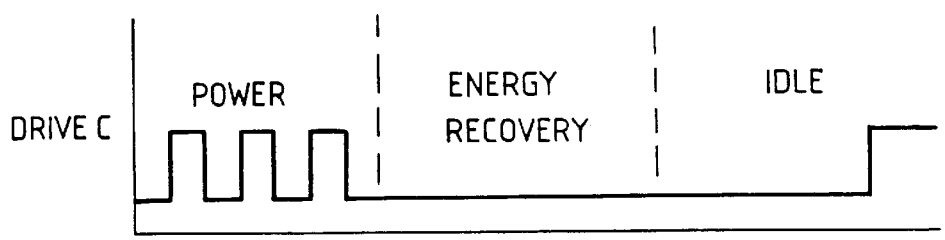
FIGS. 17A and 17B illustrate a set of waveforms for driving a DC-to-AC converter at two different frequencies and with an energy recovery mode.
Figure 17B:
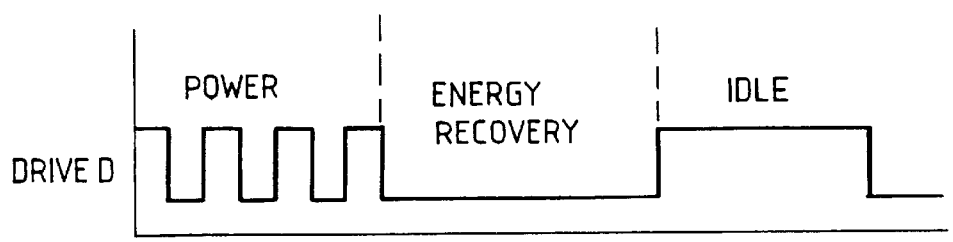

FIGS. 17A and 17B illustrate exemplary drive signals in the form of a DRIVE C signal and a DRIVE D signal. As shown, both of those drive signals are low, or logic "0," during the energy recovery period so that all four of the transistors 170–176 are turned off, and are non-conductive, during the energy-recovery period. The energy-recovery period may last, for example, about 20 microseconds or about four full cycles of the relatively high frequency used to drive the circuit 104a during the power-supply mode.

FIG. 18B illustrates the current flows that occur during ringing when the circuit 104a is in the energy-recovery mode. Referring to FIG. 18B, when the circuit 104a transitions to the energy-recovery mode, during one half-cycle of the bidirectional ringing current, current will flow from electrical ground, upwards through the diode 456, through the capacitor 148 and the external coil 150, upwards through the diode 450 and into the power source 102, as indicated by the arrow 460 shown in FIG. 18B. During the next half-cycle of the ringing current, current will flow from electrical ground, upwards through the diode 452, through the external coil 150 and the capacitor 148, upwards through the diode 454 and into the power source 102, as indicated by the arrow 462 shown in FIG. 18B.

It should be noted that, during both half-cycles of the ringing current described above in connection with FIG. 18B, current flows from electrical ground into the power source 102. Consequently, electric power is recovered by the power source 102. In contrast, during every other half-cycle of the ringing current described above in connection with FIG. 18A, current flows out of the power source 102.

Figure 19:
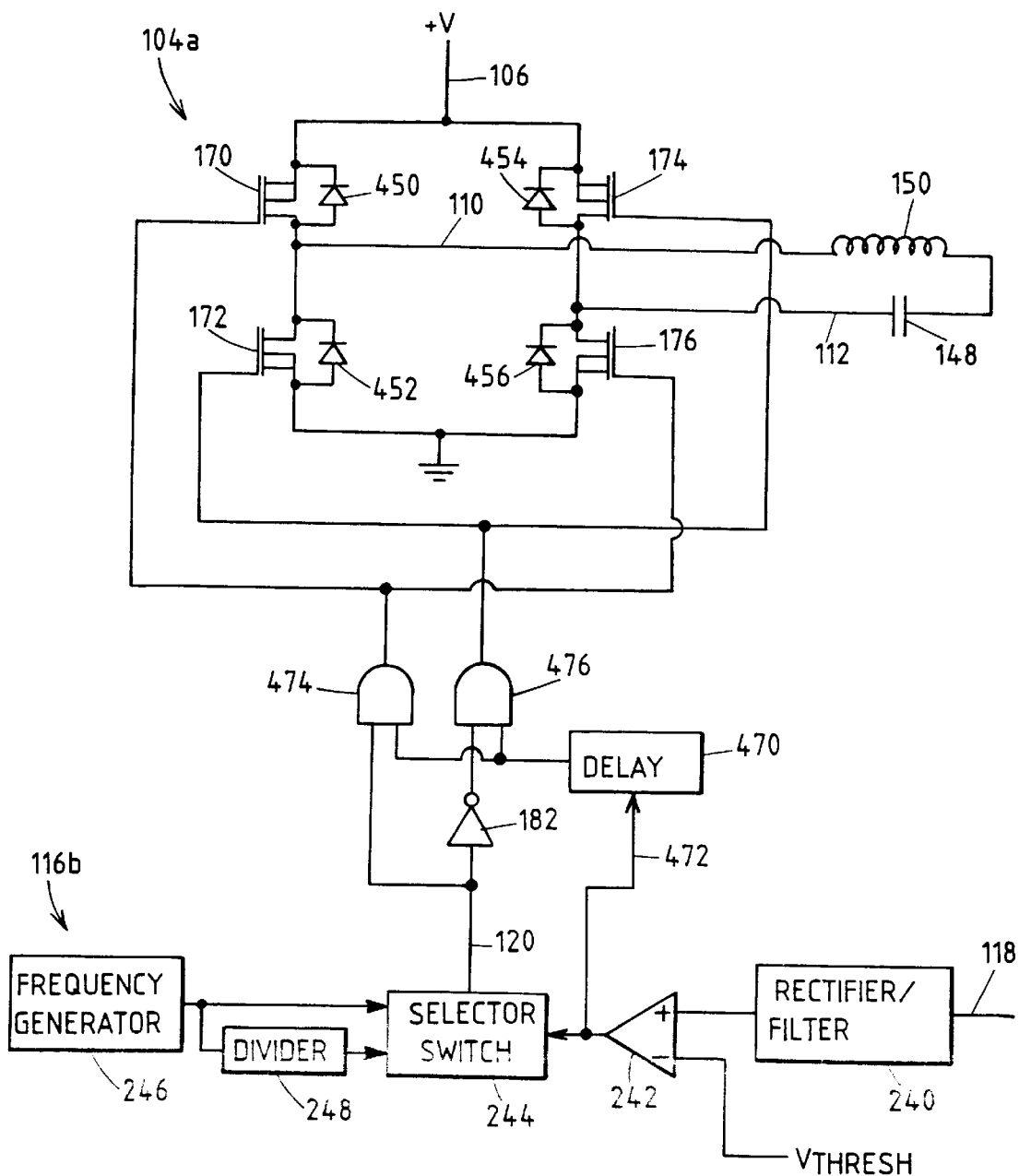
FIG. 19 illustrates an alternative embodiment of the AC-to-DC converter shown schematically in FIG. 4 and an alternative embodiment of a controller shown schematically in FIG. 5.

FIG. 19 illustrates the DC-to-AC converter 104a and a control circuit 116b, which is an alternative embodiment of the controller 116 shown schematically in FIG. 3, which may be used to drive the converter 104a in the energy-recovery mode described above.

Referring to FIG. 19, the control circuit 116b includes the rectifier/filter circuit 240, the comparator 242, the selector switch 244, the frequency generator 246 and the frequency divider 248, all of which operate as described above in connection with FIG. 5.

The control circuit 116b includes additional circuitry that is used to force the drive signals to a value, such as logic "0," that causes the transistors 170–176 to be turned off during the energy-recovery period. That additional circuitry may be provided in the form of a delay element 470, which may be a timer or one-shot, that is coupled to the output of the comparator 242 via a conductor 472. The output of the delay element 470 may be connected to one input of each of a pair of AND gates 474, 476. The drive signals output from the selector switch 244 are provided to a second input of each of the AND gates 474, 476. As described above, the comparator 242 can detect when the artificial heart assembly 10 transitions from the power-supply mode to the idle mode (in which case the output of the comparator 242 will change from logic "1" to logic "0").

Upon detecting a change in the output of the comparator 242, the delay element 470 will force the outputs of the AND gates 474, 476 to logic "0," causing all four transistors 170–176 to be turned off, by transmitting a logic "0" signal to one of the inputs of each of the AND gates 474, 476 for the time period corresponding to the energy-recovery mode.

Additional details may be disclosed in the following patent applications, for which William Weiss is the named inventor, each of which is incorporated by reference herein: U.S. Ser. No. 09/557,813 filed herewith and entitled "Artificial Heart Power Supply System"; U.S. Ser. No. 09/557,814 filed herewith and entitled "Artificial Heart With Synchronous Rectification"; U.S. Ser. No. 09/557,809 filed herewith and entitled "Artificial Heart Data Communication System"; and U.S. Ser. No. 09/557,810 filed herewith and entitled "Artificial Heart With Metal Detection."

Metal Detection

The operation of the artificial heart assembly 10 may be adversely affected if one or both of the external and internal coils 150, 152 comes relatively close to either a conductive material, such as metal, or a magnetically permeable material, such as ferrite. If such a material comes in close proximity with one of the coils 150, 152, the inductive coupling between the coils 150, 152 will be altered, thus changing the power transmission characteristics between the coils 150, 152 in an unintended and possibly adverse manner. In such case, delivery of electric power to the internal portions of the artificial heart assembly 10 may be disrupted, and the internal or external electrical components of the artificial heart assembly 10 may be damaged.

Conductive materials and magnetically permeable materials which interfere with the inductive coupling of the coils 150, 152 and their power transmission characteristics are collectively referred to herein as "interfering materials." The close proximity of an interfering material to one of the coils 150, 152 may change one or both of the inductances $L_{INT}$ and $L_{EXT}$ described above, resulting in de-tuning of the resonant circuit formed by the coils 150, 152. The close proximity of an interfering material may also alter the magnetic flux linkage between the coils 150, 152.

The artificial heart assembly 10 may be designed to detect when an interfering material comes in relatively close proximity with one of the coils 150, 152 and may be designed to cause a remedial action to be undertaken in response thereto. For example, upon detection that an interfering material is in close proximity to one of the coils 150, 152, the artificial heart assembly 10 could generate an alarm, such as a visual or audible warning, and/or could prevent power from being provided to the external coil 150.

The detection of an interfering material in proximity with one of the coils 150, 152 could be based on the detection of a phase shift between the voltage supplied by the external coil 150 and the current that passes through the external coil 150. Alternatively, the proximity of an interfering material could be based upon the detection or determination of other characteristics of one or both of the coils 150, 152, such as based on the magnitude of the current flowing through the external coil 150.

FIG. 22 is a block diagram of one possible embodiment of a detection circuit 500 that detects the proximity of an interfering material and causes one or more remedial actions to be taken in response thereto. The detection circuit 500 shown in FIG. 22 is similar to the circuit 116b shown in FIG. 19 to the extent that the detection circuit 500 includes the components 182, 240, 242, 244, 246, 248, 474 and 476, the operation of which is described above. only the new components of the detection circuit 500 are described below.

Referring to FIG. 22, the detection circuit 500 may be provided with a square-wave generating circuit, such as a zero-crossing detector 502, that is coupled to receive the signal on the line 118 generated by the current sensor 114 (FIG. 3), which signal has the same frequency and may have substantially the same phase as the current passing through the external coil 150. From the signal on the line 118, which may be generally sinusoidally shaped, the square-wave generating circuit 502 may generate a square wave having the same frequency and substantially the same phase as the signal on the line 118. The output of the circuit 502, which is representative of the frequency and phase of the current passing through the external coil 150, is provided to one input of a phase detector 504 via a line 506.

The phase of the voltage that is supplied to the external coil 150 (which may be the voltage provided across the external coil network 108) is generally the same as the phase of the logic-level signal(s) used to drive the DC-to-AC converter 104 (FIG. 3). Consequently, the output of the frequency generator 246 is representative of the phase of the voltage supplied to the external coil 150 and may be coupled to a second input of the phase detector 504 via a line 508.

The phase detector 504 may detect or determine the magnitude of the phase shift between the two signals provided via the lines 506, 508, such as by determining the time delay between the rising edge of the signal on the line 506 and the rising edge of the signal on the line 508. The phase detector 504 may provide a signal representative of the magnitude of the phase shift to a controller 510 via a line 512, and the phase detector 504 may also provide a signal representative of the phase sign to the controller via the line 512 (which may be a multi-conductor line) to indicate whether the voltage provided to the external coil 150 is leading or lagging the current (as measured) passing through the external coil 150.

In response to the signal(s) provided via the line 512, the controller 510 may take one or more remedial actions. The controller 510 may cause a visual, audible or other type of alarm or warning to be generated by activating an alarm generator 514 via a line 516. Depending on the magnitude phase shift, the controller 510 may also prevent power from being supplied to the external coil 150. That may be accomplished by transmitting a disable signal (e.g. logic "0" signal) to the AND gates 474, 476 via a line 518 to cause the transistors 170, 172, 174, 176 (FIG. 4) to become nonconductive.

The detection circuit 500 shown in FIG. 22 does not include the delay circuit 470 shown in FIG. 19, which may be used for idle-mode operation as described above. If it were desired to use both the idle-mode operation and the phase detection capability, the output of the comparator 242 could be connected to be received by the controller 510, and the controller 510 could be programmed or otherwise designed to simulate the operation of the delay circuit 470 by disabling the DC-to-AC converter 104 (via the line 518) a predetermined delay period after receiving an idle signal from the output of the comparator 242.

Figure 23:
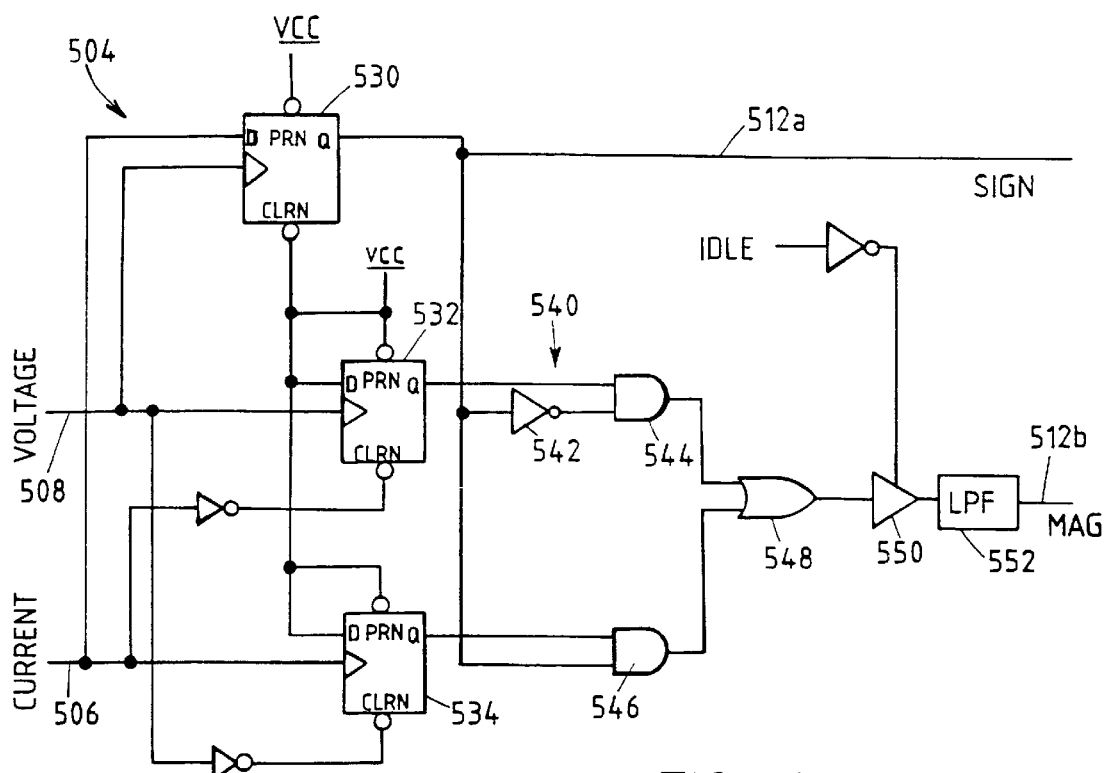
FIG. 23 is a circuit diagram of one embodiment of a phase detector shown schematically in FIG. 22.

If a phase detector is used to detect the proximity of an interfering material, the phase detector 504 shown in FIG. 23 could be utilized. Referring to FIG. 23, a signal representative of the phase of the voltage that is supplied to the external coil 150 is supplied to the phase detector 504 via the line 508, and a signal representative of or based on the phase of the current that passes through the external coil 150 is supplied to the phase detector 504 via the line 506.

The phase detector 504 may be provided with a first circuit, which may be in the form of a D flip-flop 530, that determines the sign of the phase difference between the voltage and current, i.e. whether the voltage leads or lags the current. A D flip-flop may operate by passing the value of its input (designated "D") to its output (designated "Q") upon each rising edge of a signal provided to its clock input (shown by a triangle), and by forcing its output to zero if a logic "0" signal is provided to its clear input (designated "CLRN"). The preset input (designated "PRN") of the flip-flop 530 is not utilized since it is activated by a logic "0" signal and since that input is tied to a high or logic "1" voltage (in the form of "VCC").

Figure 24A:
FIGS. 24A–24F are waveforms illustrating the operation of the phase detector of FIG. 23.
Figure 24B:
Figure 24C:

For a D flip-flop as described above, if the voltage leads the current, as shown in FIGS. 24A and 24B, the flip-flop 530 will generate a logic "0" output (as shown in FIG. 24C) since the value of the current signal is low or logic "0" at each rising edge of the voltage signal. If the voltage lags the current, the flip-flop 530 will generate a logic "1" output since the value of the current signal is high or logic "1" at each rising edge of the voltage signal.

Figure 24D:
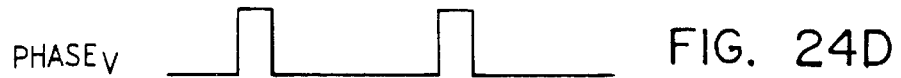

The detection circuit 504 may be provided with a D flip-flop 532 that generates a pulse having a duration corresponding to the phase difference or shift between the voltage and current when the voltage leads the current. Since the input of the flip-flop 532 is tied to a high or logic "1" voltage, the flip-flop 532 generates a high output upon the rising edge of the voltage signal on the line 508. That output falls to zero upon the rising edge of the current signal provided on the line 506 due to the current signal being provided to the clear input of the flip-flop 532. For the case where the voltage leads the current as shown in FIGS. 24A and 24B, FIG. 24D illustrates the shape of the output of the flip-flop 532, which output is designated PHASE$_V$. It can be seen that the duration or width of the PHASE$_V$ pulses corresponds to the phase difference between the voltage and current signals shown in FIGS. 24A and 24B.

Figure 24E:
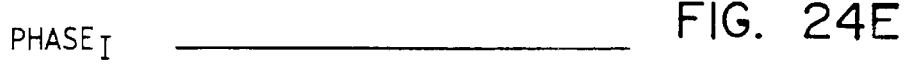
Figure 24F:
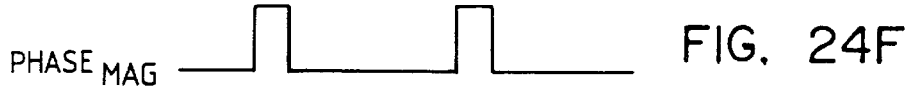

The phase detection circuit 504 may be provided with a D flip-flop 534 that operates in the same manner as the flip-flop 532 described above to determine the magnitude of the phase difference between the voltage and current in the case where the current leads the voltage. For the case where the current does not lead the voltage as shown in FIGS. 24A and 24B, FIG. 24E illustrates the shape of the output of the flip-flop 534, which output is designated PHASE$_I$, as a constant, relatively low voltage since the current does not lead the voltage. If the current did lead the voltage, the PHASE$_I$ signal would have a duration or width corresponding to the phase shift between the leading current signal and the lagging voltage signal.

The detection circuit 504 may be provided with a data selector circuit 540 in order to select either the output of the flip-flop 532 or the output of the flip-flop 534, depending on whether the voltage leads or lags the current.

The data selector circuit 540 may be composed of an inverter 542, a pair of AND gates 544, 546, and an OR gate 548. The output of the flip-flop 530, which is indicative of whether the voltage leads or lags the current, is provided to the AND gate 546, and the complemented output of the flip-flop 530 is provided to the AND gate 544. Thus, at any time, only one of the AND gates 544, 546 will be selected (by providing a logic "1" thereto) in order to provide its output to the OR gate 548. Where the voltage leads the current as shown in FIGS. 24A and 24B, the logic "0" output of the flip-flop 530 enables the AND gate 544 to cause the output ($V_{MAG}$) of the flip-flop 532 to be passed through the AND gate 544 to the OR gate 548.

The output of the OR gate 548, which represents the magnitude of the phase shift between the voltage and current, may be provided to a tri-state element or buffer 550 before being provided to a charge storage circuit, such as a low-pass filter circuit 552 having a charging capacitor (not shown). The tri-state element 550 may be used in cases where the phase detector 504 is not used all of the time.

For example, if the idle-mode feature described above is utilized, the phase detector 504 may be disabled during idle mode. In that case, an idle-mode signal indicating that the artificial heart assembly 10 is operating in the idle mode may be provided to the tri-state element 550 to cause it to enter a high-impedance state so that the value of the current phase shift magnitude signal of the charge storage circuit 552 is maintained regardless of the output of the OR gate 548. The idle-mode signal provided to the tri-state element 550 could be generated from the output of the comparator 242 (FIG. 22).

It should be understood that phase detection circuits are conventional and that there are numerous types of such circuits. Thus, the phase detection circuit shown in FIG. 23 is exemplary only and numerous other types of phase detection circuits could be utilized. Also, as noted above, detection circuits other than phase detection circuits could be utilized.

During normal operation of the artificial heart assembly 10 without an interfering material in close proximity with either of the coils 150, 152, the voltage supplied to the external coil 150 and the current that passes through the external coil 152 may have the same phase. When an interfering material comes in close proximity to one of the coils 150, the material induces a phase shift between the current and voltage. The magnitude and direction of the phase shift may depend on how close the interfering material is and whether the interfering material is closer to the external coil 150 or to the internal coil 152.

FIG. 21 illustrates a range of current-voltage phase relationships on which the operation of the artificial heart apparatus 10 may be based. In FIG. 21, a positive phase relationship is one in which the voltage leads the current, and a negative phase relationship is one where the voltage lags the current. The phase relationships shown in FIG. 21 may not represent the actual phase relationships of voltage that is supplied to the external coil 150 and the current that passes through the external coil 150 due to phase delays caused by measurement. For example, the signal generated by the current sensor 114 (FIG. 1) may be delayed somewhat in phase with respect to the actual current passing through the external coil 150. Also, the zero-crossing detector 502 may generate a signal delay. However, even with delays induced by measurement, it should be understood that the close proximity of an interfering material will cause substantially the same phase shift in the measured signals as it does in the actual current and voltage.

Still referring to FIG. 21, during operation of the artificial heart assembly 10 without an interfering material in close proximity with one of the coils 150, 152, there may be a range of normal phase relationships in which there is a given range of measured phase differences between voltage and current. Upon an interfering material coming into proximity with one of the coils 150, 152, the magnitude of the phase shift may decrease to a warning level (as indicated by a dotted line), upon which an audible or visual warning may be generated. Upon the interfering material coming into closer proximity with one of the coils 150, 152, the magnitude of the phase shift may further decrease to a fault level, upon which the supply of power to the external coil 150 may be suspended or interrupted.

Figure 25:
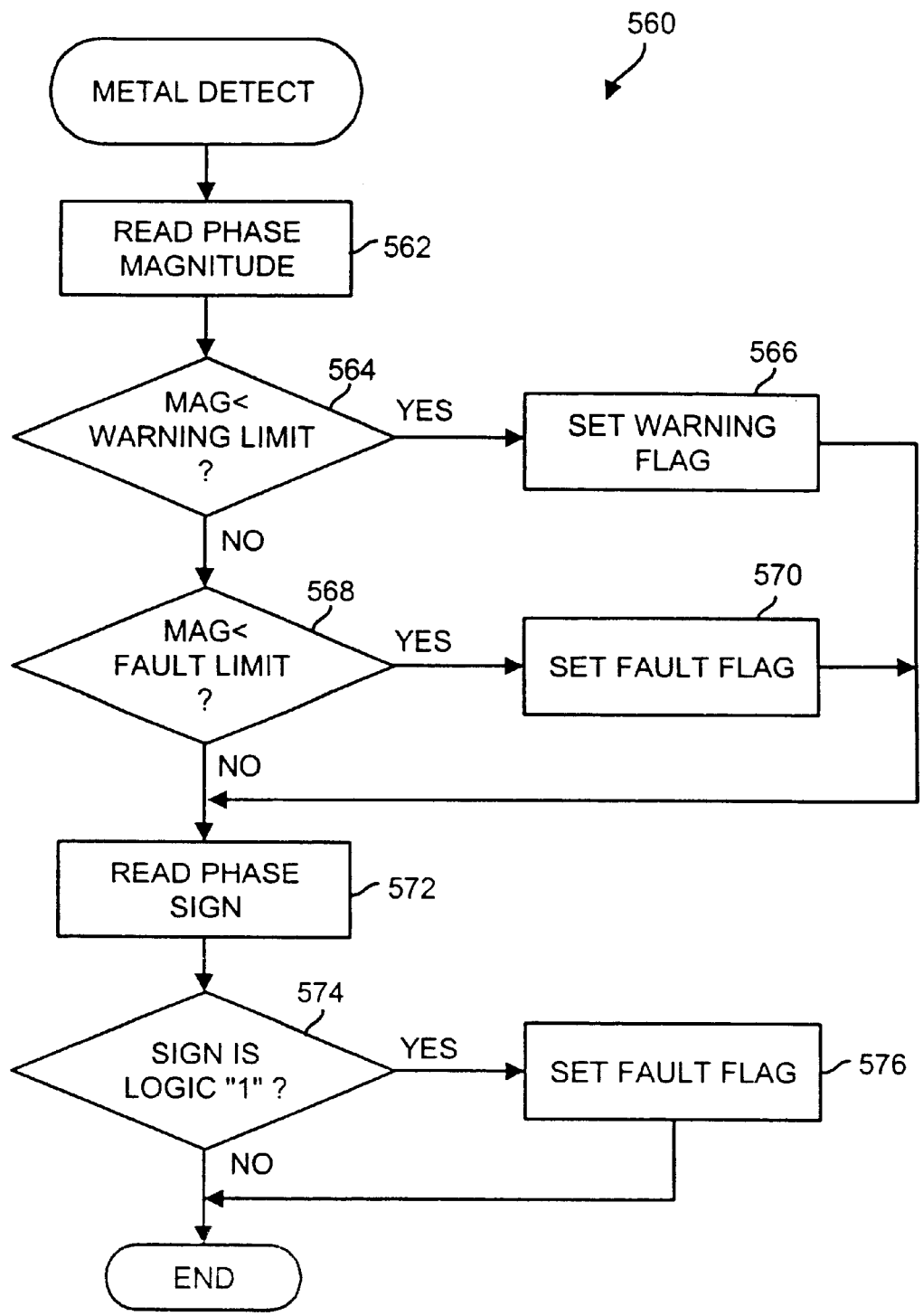
FIG. 25 is a flowchart illustrating one example of the operation of the controller shown in FIG. 22.

FIG. 25 is a flowchart of a metal detect routine 560 illustrating a number of actions that could be periodically performed (e.g. once every second) by the controller 510 shown in FIG. 22. The controller 510 could have the components shown in FIG. 20, in which case a computer program that performs the actions shown in FIG. 25 could be stored in the program memory 402 (FIG. 20) and performed by the microprocessor 403.

Referring to FIG. 25, at block 562, the magnitude of the phase difference is read by the controller 510, which phase difference may be that generated on the line 512b shown in FIG. 23. If the magnitude of the phase difference is less than a warning threshold limit as determined at block 564, the program may branch to block 566 where a warning flag may be set to cause a first type of remedial action to be performed, such as the generation of an audible or visible alarm.

If the magnitude of the phase difference read at block 562 is less than a fault threshold limit as determined at block 568, the program may branch to block 570 where a fault flag may be set to cause a second type of remedial action to be performed, such as the interruption in the supply of power to the external coil 150 (which may be accomplished via a logic "0" signal being generated by the controller 510 on the line 518 in FIG. 22).

At block 572, the sign of the phase difference may be read from the line 512a shown in FIG. 23. At block 574, if the sign of the phase difference is logic "1," meaning that the current is leading the voltage, a fault flag may be set at block 576.

It should be understood that not all actions shown in FIG. 25 are necessary, and various actions could be eliminated or modified. For example, blocks 572–576 could be eliminated and blocks 562–570 could be modified to act upon the magnitude of the current that passes through the external coil 150 instead of the phase difference between the voltage and current as described above.

Numerous additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. An artificial heart assembly, comprising:
    a blood inlet conduit;
    a blood outlet conduit;
    a pump that is adapted to pump blood from said blood inlet conduit to said blood outlet conduit;
    an internal coil adapted to be implanted beneath the skin of a subject;
    an external coil adapted to be disposed adjacent said internal coil and separated from said internal coil by the skin of a subject, said external coil being coupled to transmit electric power to said internal coil through the skin of a subject; and
    a DC-to-AC converter coupled to said external coil and to a source of DC power, said DC-to-AC converter selectively converting DC power from said DC power source into either a first frequency or a second frequency, said first frequency having a plurality of cycles each of a first duration and said second frequency having a plurality of cycles each of a second duration longer than said first duration, said DC-to-AC converter comprising:
        a first transistor coupled in parallel with a first diode;
        a second transistor coupled in parallel with a second diode;
        a third transistor coupled in parallel with a third diode;
        a fourth transistor coupled in parallel with a fourth diode; and
        a drive circuit operatively coupled to said transistors, said drive circuit causing all four of said transistors to be switched to a nonconductive state so that said four transistors are nonconductive for a time period.

2. An artificial heart assembly as defined in claim 1 wherein said drive circuit causes all four of said transistors to be switched to a nonconductive state for a time period at least as long as said first duration.

3. An artificial heart assembly as defined in claim 1 wherein said drive circuit causes all four of said transistors to be switched to a nonconductive state for a time period at least twice as long as said first duration.

4. An artificial heart assembly as defined in claim 1 wherein said DC-to-AC converter is operable in a power-supply mode and an idle mode, wherein said DC-to-AC converter converts DC power from said DC power source into said first frequency during said power-supply mode, and wherein said DC-to-AC converter converts DC power from said DC power source into said second frequency during said idle mode.

5. An artificial heart assembly as defined in claim 1 wherein said DC-to-AC converter is operable in a power-supply mode and an idle mode, wherein said DC-to-AC converter converts DC power from said DC power source into said first frequency during said power-supply mode, wherein said DC-to-AC converter converts DC power from said DC power source into said second frequency during said idle mode, and wherein said first frequency is a multiple of said second frequency.

6. An artificial heart assembly as defined in claim 1 wherein said first transistor is connected to said second transistor at a first junction, wherein said second transistor is connected to said third transistor at a second junction, wherein said third transistor is connected to said fourth transistor at a third junction, and wherein said fourth transistor is connected to said first transistor at a fourth junction.

7. An artificial heart assembly as defined in claim 6 wherein said fourth junction is connected to said DC power source, wherein said second junction is connected to a ground potential, and wherein said external coil is connected between said first and third junctions.

8. An artificial heart assembly as defined in claim 1 additionally comprising a membrane defining a blood chamber fluidly coupled to said blood inlet conduit and said blood outlet conduit, wherein said pump comprises a pusher member which makes contact with said membrane to force blood from said blood inlet conduit to said blood outlet conduit.

9. An artificial heart assembly as defined in claim 1 additionally comprising:
- a first membrane defining a blood chamber fluidly coupled to said blood inlet conduit and said blood outlet conduit, wherein said pump comprises a pusher member which makes contact with said first membrane to force blood from said blood inlet conduit to said blood outlet conduit;
- a second membrane defining a second blood chamber fluidly coupled to a second blood inlet conduit and a second blood outlet conduit; and
- a second pusher member which makes contact with said second membrane to force blood from said second blood inlet conduit to said second blood outlet conduit.

10. An artificial heart assembly, comprising:
a blood inlet conduit;
a blood outlet conduit;
a pump that is adapted to pump blood from said blood inlet conduit to said blood outlet conduit;
an internal coil adapted to be implanted beneath the skin of a subject;
an external coil adapted to be disposed adjacent said internal coil and separated from said internal coil by the skin of a subject, said external coil being coupled to transmit electric power to said internal coil through the skin of a subject; and
a DC-to-AC converter coupled to said external coil and to a source of DC power, said DC-to-AC converter selectively converting DC power from said DC power source into either a first frequency or a second frequency, said first frequency having a plurality of cycles each of a first duration and said second frequency having a plurality of cycles each of a second duration longer than said first duration, said DC-to-AC converter comprising:
  a first switching component coupled in parallel with a first passive component;
  a second switching component coupled in parallel with a second passive component;
  a third switching component coupled in parallel with a third passive component;
  a fourth switching component coupled in parallel with a fourth passive component; and
  a drive circuit operatively coupled to said switching components, said drive circuit causing all four of said switching components to be switched to a nonconductive state so that said four switching components are nonconductive for a time period and so that electric current flows through a plurality of said passive components during said time period.

11. An artificial heart assembly as defined in claim 10 wherein said drive circuit causes all four of said switching components to be switched to a nonconductive state for a time period at least as long as said first duration.

12. An artificial heart assembly as defined in claim 10 wherein said drive circuit causes all four of said switching components to be switched to a nonconductive state for a time period at least twice as long as said first duration.

13. An artificial heart assembly as defined in claim 10 wherein said first switching component is connected to said second switching component at a first junction, wherein said second switching component is connected to said third switching component at a second junction, wherein said third switching component is connected to said fourth switching component at a third junction, and wherein said fourth switching component is connected to said first switching component at a fourth junction.

14. An artificial heart assembly as defined in claim 13 wherein said fourth junction is connected to said DC power source, wherein said second junction is connected to a ground potential, and wherein said external coil is connected between said first and third junctions.

15. Apparatus for use in an artificial heart assembly having a blood inlet conduit, a blood outlet conduit, and a pump that is adapted to pump blood from the blood inlet conduit to the blood outlet conduit, said apparatus comprising:
an internal coil adapted to be implanted beneath the skin of a subject;
an external coil adapted to be disposed adjacent said internal coil and separated from said internal coil by the skin of a subject, said external coil being coupled to transmit electric power to said internal coil through the skin of a subject; and
a DC-to-AC converter coupled to said external coil and to a source of DC power, said DC-to-AC converter selectively converting DC power from said DC power source into either a first frequency or a second frequency, said first frequency having a plurality of cycles each of a first duration and said second frequency having a plurality of cycles each of a second duration longer than said first duration, said DC-to-AC converter comprising:
  a first switching component coupled in parallel with a first passive component;
  a second switching component coupled in parallel with a second passive component;
  a third switching component coupled in parallel with a third passive component;
  a fourth switching component coupled in parallel with a fourth passive component; and
  a drive circuit operatively coupled to said switching components, said drive circuit causing all four of said switching components to be switched to a nonconductive state so that said four switching components are nonconductive for a time period and so that electric current flows through a plurality of said passive components during said time period.

16. An apparatus as defined in claim 15 wherein said drive circuit causes all four of said switching components to be switched to a nonconductive state for a time period at least as long as said first duration.

17. An apparatus as defined in claim 15 wherein said drive circuit causes all four of said switching components to be switched to a nonconductive state for a time period at least twice as long as said first duration.

18. An apparatus as defined in claim 15 wherein said first switching component is connected to said second switching component at a first junction, wherein said second switching component is connected to said third switching component at a second junction, wherein said third switching component is connected to said fourth switching component at a third junction, and wherein said fourth switching component is connected to said first switching component at a fourth junction.

19. An apparatus as defined in claim 18 wherein said fourth junction is connected to said DC power source, wherein said second junction is connected to a ground potential, and wherein said external coil is connected between said first and third junctions.

* * * * *